(12) United States Patent
Yang et al.

(10) Patent No.: US 10,385,886 B2
(45) Date of Patent: Aug. 20, 2019

(54) SOFT ACTUATORS AND SOFT ACTUATING DEVICES

(71) Applicant: President and Fellows of Harvard College, Cambridge, MA (US)

(72) Inventors: Dian Yang, Cambridge, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 143 days.

(21) Appl. No.: 15/703,139

(22) Filed: Sep. 13, 2017

(65) Prior Publication Data

US 2018/0031010 A1 Feb. 1, 2018

Related U.S. Application Data

(63) Continuation of application No. 14/801,961, filed on Jul. 17, 2015, now Pat. No. 9,790,968.

(Continued)

(51) Int. Cl.
*F15B 15/10* (2006.01)
*A61F 2/08* (2006.01)
(Continued)

(52) U.S. Cl.
CPC .............. *F15B 15/103* (2013.01); *A61F 2/08* (2013.01); *A61F 2/50* (2013.01); *A61F 2/68* (2013.01);
(Continued)

(58) Field of Classification Search
CPC .. F15B 15/103; A61F 2/08; A61F 2/50; A61F 2/68; A61F 2002/5066; A61F 2002/74; A61F 2002/077; B25J 9/1075
See application file for complete search history.

(56) References Cited

U.S. PATENT DOCUMENTS 6,168,634 B1 1/2001 Schmitz
6,215,221 B1 4/2001 Cabuz et al.
(Continued)

FOREIGN PATENT DOCUMENTS

GB 2240083 A 7/1991
WO WO-2012/148472 A2 11/2012
WO WO-2014/015146 A2 1/2014

OTHER PUBLICATIONS

International Search Report and Written Opinion issued by the U. S. Patent and Trademark Office as International Searching Authority for International Application No. PCT/US2015/025603 dated Jul. 7, 2015 (8 pages).

(Continued)

*Primary Examiner* — Brian E Pellegrino
*Assistant Examiner* — Rebecca Lynee Zimmerman
(74) *Attorney, Agent, or Firm* — Wilmer Cutler Pickering Hale and Dorr LLP

(57) ABSTRACT

A soft buckling linear actuator is described, including: a plurality of substantially parallel bucklable, elastic structural components each having its longest dimension along a first axis; and a plurality of secondary structural components each disposed between and bridging two adjacent bucklable, elastic structural components; wherein every two adjacent bucklable, elastic structural components and the secondary structural components in-between define a layer comprising a plurality of cells each capable of being connected with a fluid inflation or deflation source; the secondary structural components from two adjacent layers are not aligned along a second axis perpendicular to the first axis; and the secondary structural components are configured not to buckle, the bucklable, elastic structural components are configured to buckle along the second axis to generate a linear force, (Continued)

upon the inflation or deflation of the cells. Methods of actuation using the same are also described.

23 Claims, 12 Drawing Sheets

Related U.S. Application Data

(60) Provisional application No. 62/146,463, filed on Apr. 13, 2015, provisional application No. 62/025,766, filed on Jul. 17, 2014.

(51) Int. Cl.
    *A61F 2/50*     (2006.01)
    *B25J 9/10*     (2006.01)
    *A61F 2/68*     (2006.01)
    *A61F 2/74*     (2006.01)

(52) U.S. Cl.
    CPC ..... *B25J 9/1075* (2013.01); *A61F 2002/0894* (2013.01); *A61F 2002/5066* (2013.01); *A61F 2002/74* (2013.01)

(56) References Cited

U.S. PATENT DOCUMENTS

| | | |
|---|---|---|
| 2003/0159219 A1 | 8/2003 | Harrison et al. |
| 2005/0132490 A1 | 6/2005 | Davis |
| 2007/0186712 A1 | 8/2007 | Ferraresi et al. |
| 2010/0117039 A1 | 5/2010 | Perrett et al. |
| 2014/0109560 A1* | 4/2014 | Ilievski ................ B25J 9/1075 60/327 |
| 2016/0190431 A1 | 6/2016 | Zeng et al. |

OTHER PUBLICATIONS

"Soft Robots: Make an Artificial Muscle Arm and Gripper", Instructables [online]. Sep. 6, 2012; retrieved Sep. 21, 2015, Retrieved from the internet: <https://web.archive.org/web/20120906041447/http://www.instructables.com/id/soft-robots-make-an-artificial-muscle-arm-and-gri/?allsteps>; pp. 2-3, 5-6, 8-9.

International Search Report and Written Opinion dated Oct. 19, 2015 in the international application: PCT/US15/40896, filed Jul. 17, 2015, 11 pages.

* cited by examiner

Individual BAM units with mutually independent air chamber sets

Fig. 6A
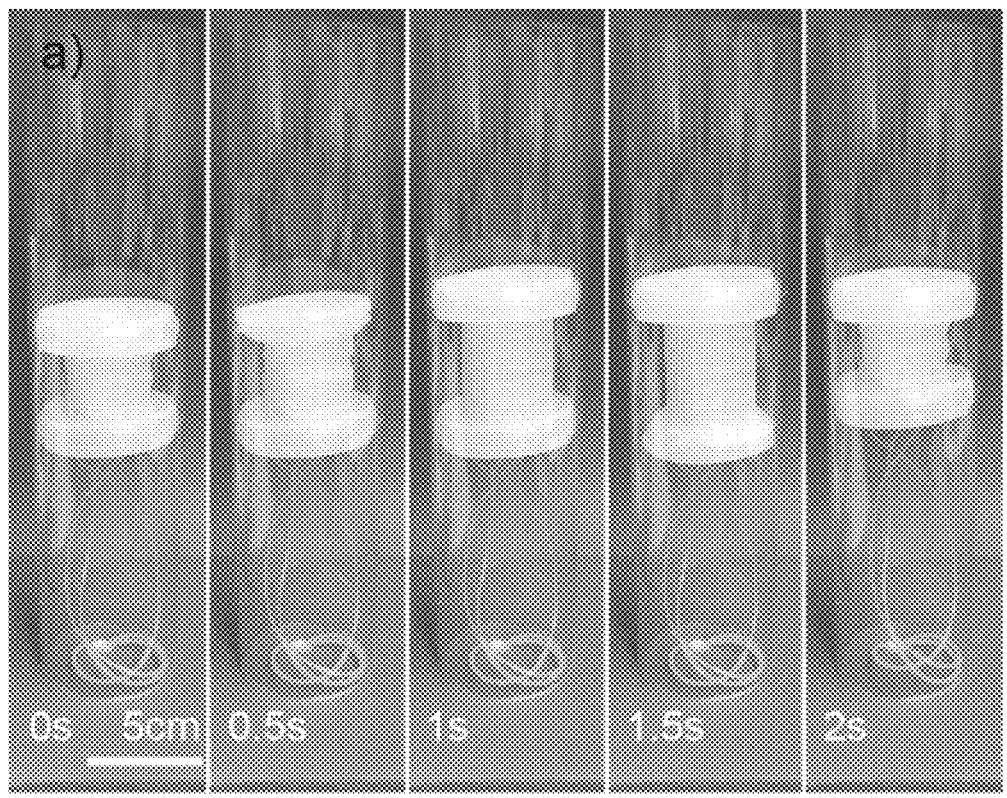
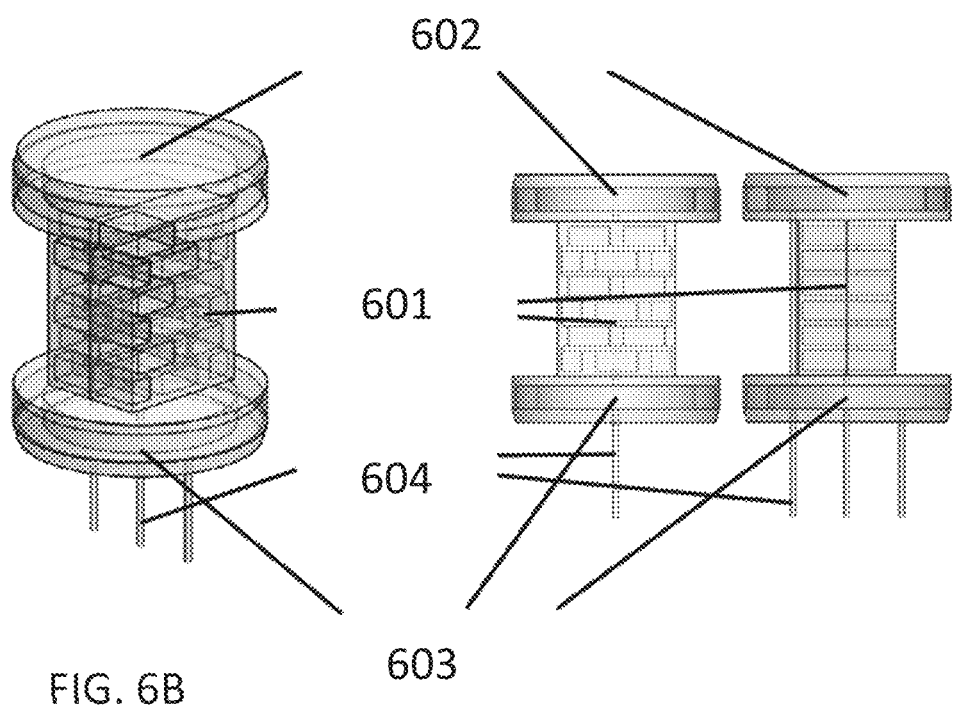
FIG. 6B

SOFT ACTUATORS AND SOFT ACTUATING DEVICES

RELATED APPLICATIONS

This application is a continuation of U.S. application Ser. No. 14/801,961, filed on Jul. 17, 2015, which claims the priority and benefits to U.S. Provisional Application No. 62/146,463, filed on Apr. 13, 2015, and to U.S. Provisional Application No. 62/025,766, filed on Jul. 17, 2014, the entire contents of which are expressly incorporated by reference.

GOVERNMENT FUNDING CLAUSE

This invention was made with support from the United States government under Grant No. DMR-0820484 awarded by the National Science Foundation, and Grant No. DE-SC0000989 awarded by the Department of Energy. The United States government has certain rights to this invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

Actuators have come a long way since the invention of rotary motors, which set the foundation for robotics and marks the dawn of the age of automation and industrialization. The drastic improvement in performance of hard actuators nowadays is only matched by the large number of emerging soft actuators, which demonstrate functionalities tantamount to or more expansive than that of their hard counterparts.

Robots or machines capable of complex movements often require many actuators working in synchrony. Such systems are potentially difficult to control. One way of reducing the complexity in control is to have parallel actuation in the system, where one or a few inputs can result in many outputs working synchronously in a desired way. For hard machines, parallel actuation can be realized through gears and levers in high precision. In soft machines, however, the counter parts of such parallel actuation systems are rare or non-existent.

"Muscle" is the almost universal actuator in animals. In efforts to mimic aspects of the mechanics of (if not the mechanism of action of) biological muscle, a large range of synthetic structures has been explored but none has successfully replicated the essential features of muscle. Muscle has three features that have remained difficult to replicate: muscle i) maintains roughly a constant volume upon contraction; ii) shows a useful compromise between speed of actuation, and force applied during actuation; iii) has mechanical properties (e.g., stiffness and density) that are compatible with the requirements of animals.

McKibben actuators, developed in the 1950s, were examples of muscle-mimetic structures. These actuators comprise a rubber balloon, surrounded by a fiber-reinforcing mesh. On pressurization, the balloon inflates anisotropically (with a motion that reflects the structure and mechanics of the surrounding mesh), and this expansion results in useful motion. The properties of the fiber reinforcement (i.e., the density of the weave, and the strength of the fibers) dictate the strain (typically 25%) and load (typically 80~130 N/cm$^2$) the actuator can produce for a given pressure. McKibben actuators have been used in many practical applications, but suffer from two major disadvantages: 1) their inherit dry friction creates heating (which changes the properties of the actuator) and hysteresis that makes precise positional control difficult; 2) they become stiff and their specific tension decreases (and approaches zero at ~25% strain) as the actuators shorten.

Soft actuators are important for their ability to contact delicate, soft, and irregularly shaped objects (i.e., humans and animals, fruit, produce), because they distribute forces across the surface of the objects, and because they are fabricated of compliant rather than unyielding materials and structures. They also offer an attractive approach to simplifying controls, since they make it possible—in some circumstances—to substitute the properties (and especially non-linearities such as "snap-through") of materials and structures for some of the control loops, sensors, and actuators of hard robots.

Pneumatically actuated soft machines are being actively developed, but, as a clan, they have two characteristics that can limit their use in some applications: i) they can burst when over-pressurized, and therefore may be dangerous or unreliable when used outside their specified operational ranges; ii) most increase in volume when pressurized, and thus cannot be used in applications in confined spaces. Thus, there remains a need for new and more effective actuators.

SUMMARY

Described herein are soft buckling linear actuators and devices, e.g., soft robotic machines and artificial skeletal muscle systems, comprising the same buckling linear actuators. The buckling linear actuator represents a new class of pneumatically driven, muscle-mimetic actuators, and can be used in machines and robots that model on structures found in anatomy. Soft actuators that are powered pneumatically are conceptually interesting and practical useful alternatives to the hard actuators used in conventional machines and robots, especially when contacting delicate objects (e.g., humans, tissue, and fruit), because they distribute forces across the surface of the objects, and because they are fabricated of compliant rather than unyielding materials and structures. They also offer an attractive approach to simplifying control systems, since they make it possible to substitute the properties of materials for some of the control loops, sensors, and actuators of hard robots.

The soft buckling linear actuator described herein includes a soft and flexible body and utilizes the buckling of one or more bucklable, elastic structural components in the actuators to generate a force, e.g., a linear force, available for actuation. The soft buckling linear actuators described herein may be actuated by deflating or over-inflating one or more cells which are inside the actuator body and structurally linked to the bucklable, elastic structural components to cause the bucklable, elastic structural component to buckle. The shape of the cell is in principle not restricted and any shape or size of the cell is contemplated.

The soft buckling linear actuator as described herein has excellent scaling capabilities, allowing easy realization of parallel actuation, e.g., using a single input or multiple inputs such as the input of pressure or vacuum to enable multiple outputs to generate synchronous movements. Thus, the soft actuating device may include a plurality of the soft buckling linear actuators to trigger multiple actuations occurring in parallel.

In certain embodiments, soft actuators that are pneumatically powered as described herein can be easily fabricated and may provide delicate object-handling capabilities (e.g., in a buckling artificial muscle) and enable sophisticated movement with the simple input of pressure. In certain embodiments, the soft buckling actuator generates forces, e.g. linear forces, as fluid is pumped in and out of the actuator's cell(s).

As used herein, "soft actuator" refers to an actuator with at least one portion of its body being soft. As used herein, "soft body" refers to the body of the soft actuator or a portion of the soft actuator that is soft, and may be involved in the actuation movement of the soft actuator. However, the soft actuator or soft body, as used herein, may have one or more portions of its body being hard or may be connected with a hard part or device.

As used herein, "structurally linked" refers to the scenario in which two structural components are connected directly, or indirectly through an additional structural component. As a result, the movement of one of the structurally linked components will result in the movement of the other component(s).

As used herein, buckling artificial muscle (BAM), also referred to as the vacuum-actuated muscle-mimetic pneumatic (VAMP) structures, is one specific example of the soft buckling linear soft actuator described herein. As used herein, buckling artificial muscle (BAM) and vacuum-actuated muscle-mimetic pneumatic (VAMP) structures are used interchangeably. As used herein, "linear buckling actuator" and "buckling linear actuator" are used interchangeably.

In one aspect, a soft buckling linear actuator is describe, including:
- a plurality of substantially parallel bucklable, elastic structural components each having its longest dimension along a first axis; and
- a plurality of secondary structural components each disposed between and bridging two adjacent bucklable, elastic structural components;

wherein
- every two adjacent bucklable, elastic structural components and the secondary structural components in-between define a layer comprising a plurality of cells each capable of being connected with a fluid inflation or deflation source;
- the secondary structural components from two adjacent layers are not aligned along a second axis substantially perpendicular to the first axis; and
- the secondary structural components are configured not to buckle, the bucklable, elastic structural components are configured to buckle along the second axis to generate a linear force, upon the inflation or deflation of the cells.

In any one of embodiments described herein, the plurality of cells are connected to each other and configured for connection with the same fluid inflation or deflation source but are otherwise isolated from the atmosphere.

In any one of embodiments described herein, the secondary structural components from two adjacent layers are not aligned along their longest dimensions.

In any one of embodiments described herein, a secondary structural component of a first layer is positioned above a cell of an adjacent, second layer and a secondary structural element of the second layer is positioned below a cell of the first layer.

In any one of embodiments described herein, the linear force is an expansion or contracting force.

In any one of embodiments described herein, the first axis is horizontal and the second axis is vertical.

In any one of embodiments described herein, the bucklable, elastic structural component is one of the walls of the cell.

In any one of embodiments described herein, the bucklable, elastic structural component is configured to buckle upon the deflation of the cell and return to its original position when the deflated cell is re-inflated.

In any one of embodiments described herein, the bucklable, elastic structural component is configured to buckle upon the deflation of the cell to generate a contracting force.

In any one of embodiments described herein, the bucklable, elastic structural component is configured to buckle upon the over-inflation of the cell which generates a pressure above the atmosphere pressure and returns to its original position when the over-inflated cell is deflated.

In any one of embodiments described herein, the bucklable, elastic structural component is configured to buckle upon the over-inflation of the cell to generate an expansion force.

In any one of embodiments described herein, the bucklable, elastic structural component has high aspect ratio.

In any one of embodiments described herein, the secondary structural component is one of the walls of the cell.

In any one of embodiments described herein, the secondary structural component has its long dimension along the second axis.

In any one of embodiments described herein, the secondary structural component is thicker, shorter and/or more rigid than the bucklable, elastic structural component.

In any one of embodiments described herein, the fluid is a gas or liquid.

In any one of embodiments described herein, the fluid is air.

In any one of embodiments described herein, the cell is connected to a gas inflation/deflation source via a fluid chamber.

In any one of embodiments described herein, the cell is in the form of a rod, slit, sphere, cube, hexahedron, or cylinder.

In any one of embodiments described herein, the bucklable, elastic structural component is in the form of a pillar, a lever, or beam.

In any one of embodiments described herein, the cells are connected to a fluid chamber configured for connection with the fluid inflation or deflation source.

In any one of embodiments described herein, the fluid inflation or deflation source is a gas pump, a gas vacuum, or a gas pump and vacuum.

In any one of embodiments described herein, the soft buckling linear actuator further includes a hard body portion.

In another aspect, an artificial skeletal muscle system is described, including:
- one or more artificial skeletal elements; and
- a soft buckling linear actuator described in any embodiment herein and connected to the artificial skeletal element;

wherein upon the inflation or deflation of the cells, the soft buckling linear actuator generates a linear force so that the artificial skeletal element performs a human or animal-like motion.

In any one of embodiments described herein, the artificial skeletal muscle system is an artificial limb, finger, toe, heart, or stomach.

In yet another aspect, a soft robotic machine is described, including:

a soft machine element; and a soft buckling linear actuator described in any embodiment herein and connected to the soft machine element, wherein upon the inflation or deflation of the cells, the soft buckling linear actuator generates a linear force so that the soft machine moves to mimic a human or animal-like motion or structure.

In any one of embodiments described herein, the soft robotic machine is a soft robotic millipede or climber.

In any one of embodiments described herein, the soft machine element is another soft buckling linear actuator, a hard or soft body part, or a pneumatic expansion actuator.

In any one of embodiments described herein, the soft robotic machine has a whole soft body or a predominantly soft body.

In any one of embodiments described herein, the soft buckling linear actuator is configured to generate a contracting force or an expansion force.

In yet another aspect, a method of actuation is described, including:

providing the soft buckling linear actuator described in any embodiment herein; and deflating the cells or over-inflating the cells to cause the bucklable, elastic structural component to buckle to generate a linear force.

In any one of embodiments described herein, the method further includes causing the soft buckling linear actuator to expand or contract.

In any one of embodiments described herein, causing the soft buckling linear actuator to expand comprises over-inflating the cell(s) to cause the bucklable, elastic structural component to buckle to generate an expansion force.

In any one of embodiments described herein, causing the soft buckling linear actuator to contract comprises deflating the cell(s) to cause the bucklable, elastic structural component to buckle to generate a contracting force.

In yet another aspect, a method of actuation is described, including:

providing the artificial skeletal muscle system of any embodiment described herein; and independently deflating or over-inflating the cells of the plurality of the soft buckling linear actuators to cause the bucklable, elastic structural components to buckle to generate linear forces and the artificial skeletal muscle system to move to mimic a human or animal-like motion or structure.

In any one of embodiments described herein, the method further includes causing the soft buckling linear actuators to expand or contract.

In yet another aspect, a method of actuation is described, including:

providing the soft robotic machine of any embodiment described herein; and independently deflating or over-inflating the cells of the plurality of the soft buckling linear actuators to cause the bucklable, elastic structural components to buckle to generate linear forces and the soft machine to move to mimic a human or animal-like motion or structure.

In any one of embodiments described herein, the method further includes causing the soft buckling linear actuators to expand or contract.

It is contemplated that any embodiment disclosed herein may be properly combined with any other embodiment disclosed herein. The combination of any two or more embodiments disclosed herein is expressly contemplated.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein.

It will be understood that the spatially relative terms, as well as the illustrated configurations, are intended to encompass different orientations of the apparatus in use or operation in addition to the orientations described herein and depicted in the figures. Spatially relative terms, such as "above," "below," "left," "right," "in front," "behind," and the like, may be used herein for ease of description to describe the relationship of one element to another element, as illustrated in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "linked to," "on," "connected to," "coupled to," "in contact with," etc., another element, it may be directly linked to, on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

DESCRIPTION OF THE DRAWINGS

The invention is described with reference to the following figures, which are presented for the purpose of illustration only and are not intended to be limiting. In the Drawings:

FIG. 3A shows a BAM of the same geometry as in FIG. 1C, but made of Elastosil silicone rubber as lifting a heavier weight (500 g), according to one or more embodiments described herein. FIG. 3B shows a BAM of the same geometry, but made of Stratasys PolyJet 3D printed soft material (E~1.6 MPa) which lifts an even heavier weight (~2.3 kg plus metal basket), according to one or more embodiments described herein.

FIG. 6A shows a tube-climbing robot including a buckling linear actuator sandwiched between two pneumatically actuated buckling linear expanding actuators and the snapshots of its movement, according to one or more embodiments described herein. FIG. 6B provides a schematic illustration of this tube-climbing robot that has both buckling actuators and pneumatic expansion actuators, according to one or more embodiments described herein.

DETAILED DESCRIPTION

Figure 1A:
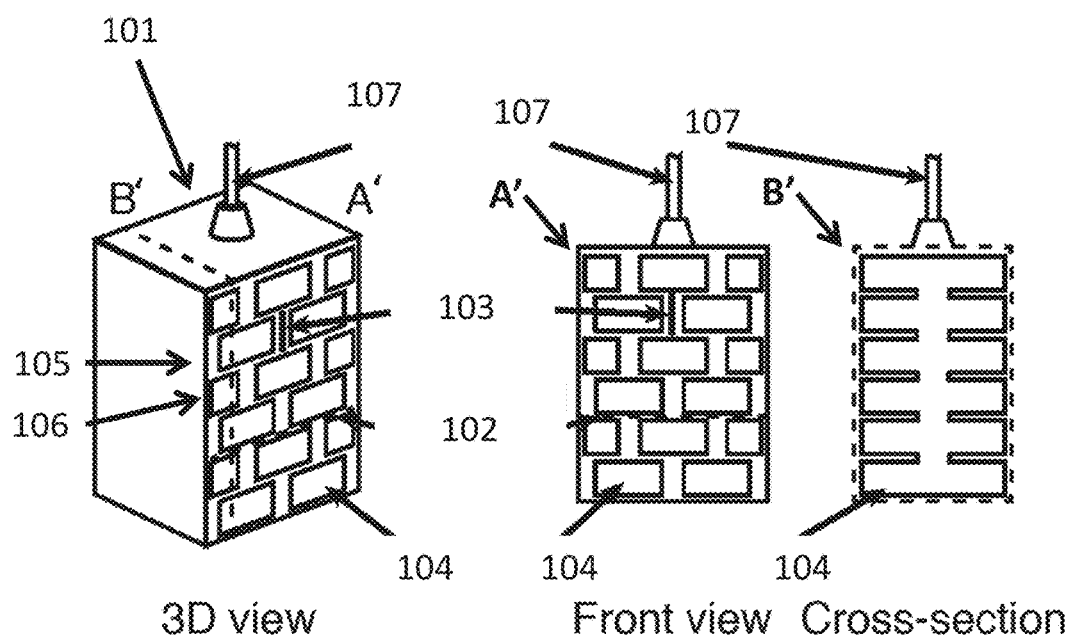
FIG. 1A shows 3D, front and cross-sectional schematics of a vacuum-actuated muscle-mimetic pneumatic (VAMP) structure including an elastomeric structure of vertical walls, thinner horizontal walls, and connected air chambers and actuated using a single external port and a source of vacuum, according to one or more embodiments described herein.

In one aspect, a soft buckling linear actuator is described, including: a plurality of substantially parallel bucklable, elastic structural components each having its longest dimension along a first axis; and a plurality of secondary structural components each disposed between and bridging two adjacent bucklable, elastic structural components; wherein every two adjacent bucklable, elastic structural components and the secondary structural components in-between define a layer comprising a plurality of cells each capable of being connected with a fluid inflation or deflation source; the secondary structural components from two adjacent layers are not aligned along a second axis perpendicular to the first axis; and the secondary structural components are configured not to buckle, the bucklable, elastic structural components are configured to buckle along the second axis to generate a linear force, upon the inflation or deflation of the cells. In certain embodiments, the secondary structural components from two adjacent layers are not aligned along their longest dimensions.

As used herein, "horizontal" is an internal reference and indicates that the elastic bucklable elements are arranged in a plane that is arbitrarily defined as "horizontal". "Horizontal" provides a frame of reference to describe the position of the elastic bucklable elements relative to other elements of the linear actuator, such as the secondary structural elements. As used herein, the phrase "approximately horizontal" refers to the scenario in which two adjacent bucklable, elastic structural components are at 180 degrees, or 165, 170, 175, 176, 178, or 179 degrees or from 165-180 degrees, from 170-180 degrees, or 175-180 degrees. As used herein, the phrase "substantially parallel" refers to the scenario in which two adjacent bucklable, elastic structural components are at 180 degrees, or 165, 170, 175, 176, 178, or 179 degrees or from 165-180 degrees, from 170-180 degrees, or 175-180 degrees.

In some embodiments, the bucklable, elastic structural component has a high aspect ratio and is configured to buckle upon the deflation or inflation of the cell along an axis about perpendicular to its long dimension (also referred to as "the first axis") to generate a linear force available for actuation. In some embodiments, the soft buckling linear actuator comprises a plurality of layers each comprising a plurality of cells. The layers include at least two adjacent layers, a first cell layer and a second cell layer. In certain embodiments, the cells in two adjacent rows are not aligned along the direction of the linear force, that is, they are offset. In certain specific embodiments, a secondary structural component of the first layer is positioned above a cell of the second layer and a secondary structural element of the second layer is positioned below a cell of the first layer (see, FIGS. 1A-1C).

As used herein, the term "buckle" refers the phenomenon in which a structural component of the soft actuator bends or collapses when induced by a compressive force on this component. In certain embodiments, "buckling" happens when the fluidic chambers in the soft device are deflated, as deflation (but not limited to) of structures lead to overall or local compression and compressive forces. Thus, a bucklable, elastic structural component is an elastic structural component of the soft actuator that is capable of bending or collapsing under certain circumstances (often under circumstances when the actuator is deflated). In certain embodiments, the bucklable, elastic structural components are in the form of pillars, levers, or beams. As used herein, the term "pillar", "lever", and "beam" all refer to a structure that has two ends, which, under a compressive force applied across the two ends, can either buckle, or resist a compression and maintain its shape to some extent but will buckle under the pressure. In certain embodiments, those pillars/levers/beams that buckles have higher aspect ratio than those that maintain their shapes, thanks to Euler's buckling formula.

The soft buckling linear actuator's soft body contains a plurality of cells inside the soft body. As used herein, the term "cell" refers to an enclosed space within the soft body of the soft buckling linear actuator. The cells are configured for connection with an external fluid inflation and/or deflation source. The geometry of the cell can take on any form or shape. In some embodiments, the cell is in the form of a rod, slit, triangular prisms, square prisms, spheres, rectangular prisms cylinder or a cylinder of oval cross-section shape. In certain embodiments, other than the connection to the fluid inflation and/or deflation source, the cell is isolated from the outside atmosphere. In some embodiments, the cells are all connected to the same fluid source. In other embodiments, at least two of the cells are connected to different fluid sources so that the two or more cells may be vacuumed/inflated independently by controlling the different fluid sources. In certain embodiments, two or more cells are connected to each other. The soft body or portions thereof define the boundaries, e.g., walls, of the cells. In certain embodiments, the bucklable, elastic structural component makes up at least one of the boundaries, e.g., walls, of the cell. In certain embodiments, the bucklable, elastic structural component and the secondary structural component (described further below) make up two or more boundaries, e.g., walls, of the cell.

In some embodiments, the soft actuating device further includes one or more secondary structural components structurally linked to the cell, wherein the secondary structural component does not buckle upon the deflation or inflation of the cell, or is designed not to buckle first. The secondary structural component can be directly attached or adjacent to the cell or connected to one or more additional structural elements which are directly attached or adjacent to the cell. In certain embodiments, the secondary structural component does not buckle when the bucklable, elastic structural component buckles as a result of the deflation or over-inflation of the cell. In certain embodiments, the secondary structural component is made from a non-elastic material or a material that is less elastic than the material of the bucklable, elastic structural component. In other embodiments, the secondary structural component is made from a material the same as or similar to the material of the bucklable, elastic structural component but is thicker and/or shorter and thus is more resistant to pressure. The secondary structural component can be in any form or shape, e.g., (in the case of BAM) a pillar, a beam, or a column (or any polyhedron or smooth 3D shape in general). As a result, when the cell is deflated or over-inflated, the secondary structural component remains in the same position/shape and the bucklable, elastic structural component buckles to generate a linear force for actuation. In certain embodiments, the secondary structural component has a second axis along its long dimension and the bucklable, elastic structural component buckles in a direction parallel to the second axis. In certain embodiments, the bucklable, elastic structural component has a first axis along its long dimension perpendicular to the second axis, or substantially perpendicular to the second axis, i.e., about 90 degrees to the second axis (e.g., from 80-90, 85-90, 85, 86, 87, 88, 89 or 90 degrees). As used herein, "perpendicular" means two axes are at 90 degree to each other. Non-limiting examples of the angles include 70, 75, and 80, or in any range bounded by any two values of the angles are disclosed herein. While large deviations from 90 degree will hinder the ability of the bucklable component to buckle, variations can be made to enable alterations of the overall geometry from being purely rectangular. For example, for certain applications, one may want to reshape the BAM into a spindle shape to mimic that of a human muscle. In that case, one may deform/curve the vertical wall near the ends of the BAM slightly as well to accommodate the overall shape change. A non-limiting exemplary embodiment is shown in FIG. 1B, where the bucklable, elastic structural component 111 has long aspect ratio and will buckle to generate linear actuation along the direction of a, which is perpendicular to its long axis a'.

When the cell collapses during deflation/over-inflation, the bucklable, elastic structural component is subjected to forces as a result of the cell's collapse and therefore buckles. In certain embodiments, this buckling results in a change in the shape and/or size of the soft actuator's body and generates a force, e.g., a linear force, which can be utilized for actuation. Therefore, as described herein, buckling of the bucklable, elastic structural component can be used as a mechanism for actuation.

The force generated is a linear force. In some embodiments, upon the deflation or inflation of the cell, the bucklable, elastic structural component buckles, while the overall structure collapse linearly as a result of the negative pressure applied to the inside of the cell's. As a result of the vacuum of the deflation source, at least a portion of the soft actuator's body to move linearly, thus generating a linear force. The linear force may be a contracting force, or an expansion force (if a pressure is applied instead).

The bucklable, elastic structural component is structurally linked to the cell. Thus, the bucklable, elastic structural component can be directly attached or adjacent to the cell (e.g., the bucklable, elastic structural component is one of the walls of the cell), or the bucklable, elastic structural component is connected to one or more additional structural elements which are directly attached or adjacent to the cell. Thus, when the cell collapses or is over-inflated to generate a pressure, the additional structural element transfers the pressure to the bucklable, elastic structural component and causes it to buckle to generate a motion. The additional structural element may be made from a material which is not bucklable or less bucklable than the bucklable, elastic structural component. Alternatively, the additional structural element can be thicker and/or shorter than the bucklable, elastic structural component and thus will not buckle or will not buckle first. In some embodiments, the structural element may be made from one or more elastomer. Any elastomer known in the art may be used. In some embodiments, some structural elements may be made from hard materials. Any rigid materials known in the art may be used, as long as they can establish mechanical connection with the soft material used.

The soft buckling linear actuator further includes one or more secondary structural components structurally linked to the cell, wherein the secondary structural component does not buckle upon the deflation or inflation of the cell, or is designed not to buckle first. The secondary structural component can be directly attached or adjacent to the cell or connected to one or more additional structural elements which are directly attached or adjacent to the cell. In certain embodiments, the secondary structural component does not buckle when the bucklable, elastic structural component buckles as a result of the deflation or over-inflation of the cell. In certain embodiments, the secondary structural component is made from a non-elastic material or a material that is less elastic than the material of the bucklable, elastic structural component. In other embodiments, the secondary structural component is made from a material the same as or similar to the material of the bucklable, elastic structural component but is thicker and/or shorter and thus is more resistant to pressure. The secondary structural component can be in any form or shape, e.g., a pillar, a lever, or a column. As a result, when the cell is deflated or over-inflated, the secondary structural component does not buckle, and the bucklable, elastic structural component buckles to generate a force for actuation.

In some embodiments, the bucklable, elastic structural component has a high aspect ratio. As used herein, aspect ratio refers to the ratios of the long dimension to the short dimension of an object or particles. An aspect ratio of more than one is generally referred to as high aspect ratios. In certain embodiments, the bucklable, elastic structure component has an aspect ratio of more than 1:1, 2:1, 3:1, 4:1, 5:1, 10:1, or 20:1, or in the range denoted by any two values described herein. Other suitable high aspect ratios are contemplated. In certain embodiments, the bucklable, elastic structure component with a high aspect ratio may buckle in the direction perpendicular to its long dimension (see, e.g., FIGS. 1B and 1C). In other embodiments, the bucklable, elastic structure component with a high aspect ratio may buckle in the direction about 90 degrees (e.g., from 80-90, 85-90, 85, 86, 87, 88, 89 or 90 degrees) to its long dimension.

Figure 1B:
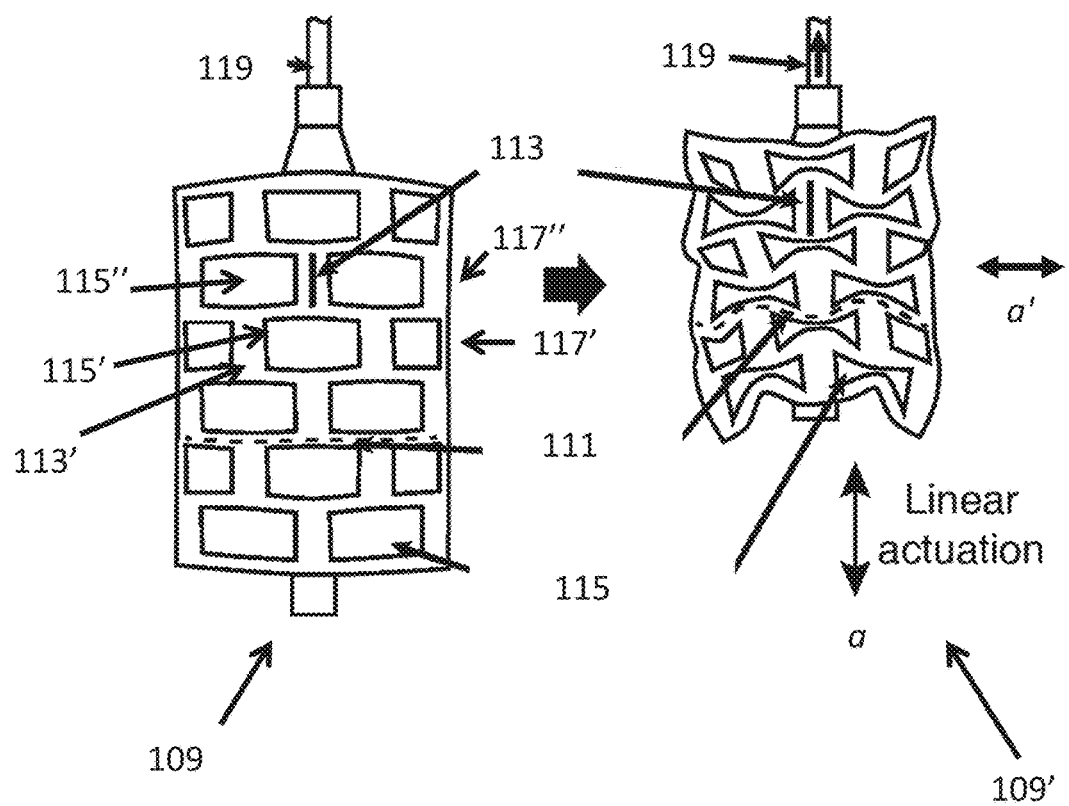
FIG. 1B shows the cross-sectional schematics of the linear actuation mechanism of a vacuum-actuated muscle-mimetic pneumatic (VAMP) structure where vacuum allows ambient pressure to compress the structure and cause the thinner horizontal walls to buckle into serpentine shapes to cause the structure to anisotropically compress in one preferred direction, according to one or more embodiments described herein.
Figure 1C:
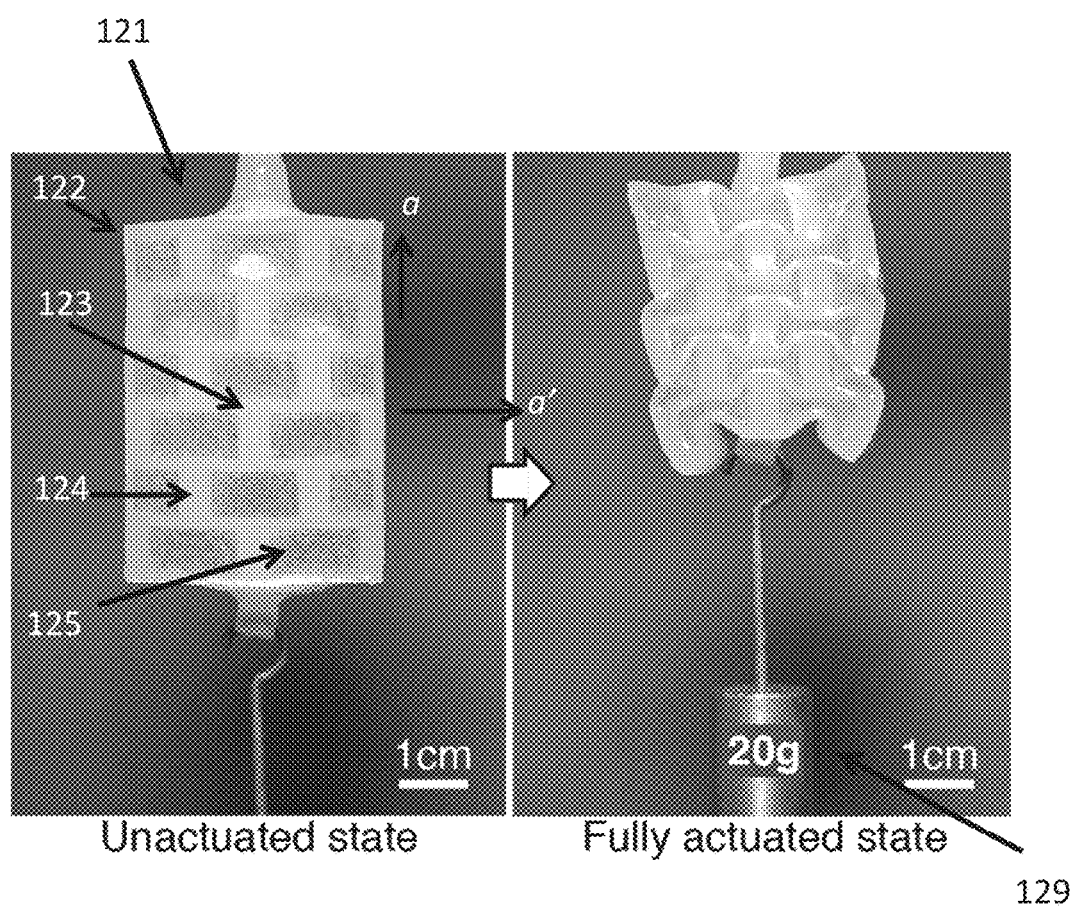
FIG. 1C shows images of a VAMP made of Ecoflex (E=43 kPa) lifting a small weight (20 g) when actuated by applying a vacuum (the inside of the chamber membranes of this VAMP is colored with a black marker, such that the boundaries of the chambers are more visible in the actuated state), according to one or more embodiments described herein.

A non-limiting exemplary embodiment of the soft buckling linear actuator is shown in FIGS. 1A-1C. As shown in FIG. 1A, a soft buckling linear actuator 101 has pattern including bucklable, elastic structural components, e.g., long, thin (1.5 mm) horizontal beams 102, bridged by secondary structural components, e.g., thick (4 mm) vertical walls 103. The details of fabrication are summarized in FIG. 7 below. Horizontal beams 102 are substantially parallel to one another and bridged by vertical beams 103, which define a plurality of cells 104. The plurality of cells 104 are connected to tube 107, connectable to a pneumatic/vacuum input. The two adjacent beams 102 and respective bridging beams 103 together a structural layer, e.g., layer 105 or 106. When a pneumatic/vacuum input is applied to the soft buckling linear actuator via tube 107, the horizontal walls 102 buckle reversibly into serpentine shapes, and these buckling actions results in a large change in the vertical length of the structure (~40%), but a negligible change in its horizontal width. FIG. 1A also shows the 3D view (left), the front view (middle; along plane A'), and the cross-section view (right; along plane B') of the soft buckling actuator 101.

FIG. 1B shows the schematics of a soft buckling linear actuator during actuation, i.e., the unactuated state 109 and the actuated state 109'. As shown in FIG. 1B, parallel bucklable, elastic structural components 111 (disposed along its longest dimension a', i.e., horizontally) and the secondary structural components 113 (disposed along an axis a which is perpendicular to the axis a') form the walls of cells 115. In certain embodiments, the bucklable, elastic structural components 111 have high aspect ratios. The secondary structural components 113 may be thicker and/or short than 111. Note that in this example, the cells 115' and 115" from two adjacent cell layers 117' and 117", respectively, are not aligned horizontally: the secondary structural component 113 of the first layer 117" is positioned above the cell 115' of the second layer 117" and the secondary structural element 113' of the second layer 117" is positioned below the cell 115" of the first layer 117". As a result, the soft body as a whole contracts linearly. Specifically, when vacuum is applied to tube 119 (which is connected to the cells 115, 115', and 115"), these cells collapse and thus the bucklable, elastic structural components 111 will buckle preferentially. The bucklable, elastic structural component 111 buckles and moves along axis a (which is about perpendicular to its long dimension) linearly while the soft actuator body contracts linearly. The secondary structural components 113 do not buckle or do not buckle first.

FIG. 1C shows a soft buckling linear actuator 121 lifting a weight 129 (Scale bars are 1 cm). As shown in FIG. 1C, a soft buckling linear actuator 121 has a soft body 122. The soft body 122 has parallelly disposed, bucklable, elastic structural components 123 and the secondary structural components 124, which form the walls of cells 125. The bucklable, elastic structural components 123 have high aspect ratios and a long dimension a'. The bucklable, elastic structural components 123, not the thicker and shorter secondary structural components 124, will buckle preferentially upon the deflation of cell 125. The bucklable, elastic structural component 123 buckles and moves along axis a (which is about perpendicular to its long dimension a' and parallel to the long axis of the secondary structural component 124) linearly and forces the soft actuator body to contract linearly, thus lifting a weight 129.

In other embodiments, upon the over-inflation of the cell (e.g., a slit), the bucklable, elastic structural component buckles linearly, i.e., expands linearly, as a result of the pressure of the cell's changed shape. The movement, i.e., linear buckling, of the bucklable, elastic structural component forces at least a portion of the soft actuator's body to expand linearly, thus generating a linear expanding force.

Buckling of materials is often considered an undesired behavior as it often results in permanent altered states of the materials that degrade their original functions. The reversible buckling of elastomeric materials as described herein, however, is free of such problems, and enables the development of a new class of actuators that utilize buckling for actuations as described herein. Thus, in some embodiments, the bucklable, elastic structural component buckles upon the deflation of the cell and returns to its un-buckled state upon re-inflation of the cell. In other embodiments, the bucklable, elastic structural component is configured to buckle upon the over-inflation of the cell, which generates a pressure above the atmosphere pressure and returns to its original position/state when the over-inflated cell is deflated. The bucklable, elastic structural component can be in any form or shape. In some specific embodiments, the bucklable, elastic structural component is in the form of a pillar, a lever, or a column. In general, the bucklable, elastic structural component can have a variety of different shapes. For example, any shape that has two ends to which a compressive force can be applied and possibly collapse the structure, such as: a banana shape, a star shape (pick any two ends), a diamond shape with a hole in the middle, etc.

Any known elastic material can be used to make the bucklable, elastic structural component. In some embodiments, the material for making the bucklable, elastic structural component is an elastic polymer. Any elastic polymer known in the art can be used. Non-limiting examples of the elastic polymer include natural rubber, silicone rubbers, polyurethane rubbers, isoprene rubber, butadiene rubber, butyl rubber, styrene-butadiene rubber, nitrile rubber, ethylene propylene rubber, epichlorohydrin rubber, polyacrylic rubber, fluorosilicone rubber, fluoroelastomers, perfluoroelastomers, polyether block amides, chlorosulfonated polyethylene, ethylene-vinyl acetate, thermoplastic elastomers, proteins resilin and elastin, polysulfide rubber, elastolefin, etc. In some embodiments, the material to make the bucklable, elastic structural component is Ecoflex, Stratasys PolyJet 3D printed soft material, Elastosil, PDMS, or another material that is elastic and airtight.

The external fluid inflation or deflation source can be any apparatus that inflates and/or deflates the fluid. Non-limiting examples of the fluid inflation or deflation sources include a gas pump, a gas vacuum, a gas pump and vacuum, a liquid pump, a liquid-suction pump, or a liquid pump and suction pump. In some embodiments, the one or more cells are connected directly to the fluid inflation/deflation source or via a fluid chamber. The use of any fluid, gas or liquid, is contemplated, including air, gas, water, oil, liquid metal. A non-limiting example of the gas is air. In some specific embodiments, the one or more cells are connected to a gas chamber, which may be connected to the gas inflation/deflation source. In other embodiments, the cell is connected to the gas inflation/deflation source directly. The use of other gases is contemplated.

In certain embodiments, the fluid is gas and the fluid inflation/deflation source is a gas inflation/vacuum source. The external gas inflation source may be a pump, gas cylinder or balloon. The external vacuum source may be a vacuum pump. Any other gas inflation source and vacuum source known in the art are contemplated.

Thus, in some embodiments, an external deflation source, e.g., vacuum source, is used to induce a negative pressure within the cell, which allows the atmospheric pressure to apply an isotropic compressive force. Pneumatic actuation using air has the additional advantages, e.g., that the air it uses is widely available, safe to operate, transfers quickly through tubing (due to its low viscosity), lightweight, and easily controlled and monitored by regulators, valves, and sensors. In some embodiments, the cells are sealed so that it is topologically closed except for the entrance into the inflation/deflation device or the common air chamber. By connecting the cells and attaching a gas channel, e.g., a tube, to the inflation/deflation device, the cells inside the soft actuator body can be inflated and deflated through pumping air and applying vacuum. In other embodiments, an external inflation source may be used to induce a positive pressure within the cell (a gas cylinder which pumps gas into a cell), which allows the cell to expand to generate a force to cause the bucklable, elastic structural component to un-buckle (pressure reverses motion).

In some embodiments, the soft buckling linear actuator comprises more than one cell connected to each other and to the fluid inflation or deflation source but otherwise isolated from the outside atmosphere. In certain embodiments, the cells are connected to the same external fluid inflation or deflation source. In other embodiments, the cells are connected to different external fluid inflation or deflation source and can be inflated or deflated (and thus actuated) independent of each other. Thus, the cells can be separate from one another, providing more degrees of freedom of actuation. For example, in certain specific embodiments, two soft buckling linear actuators (each with connected cells) can be glued (e.g., with elastomer) side-to-side, thus providing two separately controllable actuating units.

In another aspect, a soft actuating device comprising a plurality of the soft buckling linear actuator of any one of the embodiments described herein or any combination of the embodiments described herein is described. The cells can be connected to the same external fluid or vacuum source, or at least two of the soft buckling linear actuators are connected to different external fluid or vacuum sources capable of being activated independently. As a result, parallel or independent actuation is achieved.

In another aspect, an artificial skeletal muscle system is described, including:
one or more artificial skeletal elements; and
a soft buckling linear actuator of any one of the embodiments described herein and connected to the artificial skeletal element;
wherein upon the inflation or deflation of the cells, the soft buckling linear actuator generates a linear force so that the artificial skeletal element moves in a human or animal-like motion.

In certain embodiments, the artificial skeletal muscle system is an artificial limb, finger, toe, heart, stomach, or any other human or animal muscle system or muscle mimicking system. In certain embodiments, the artificial skeletal element is an artificial bone or any part of the human or animal skeleton.

In certain embodiments, the artificial skeletal muscle system is an artificial limb, including: an optionally hard artificial limb element; and a soft buckling linear actuator connected to an artificial limb element, comprising: a soft body defining a plurality of cells housed inside the soft body, the cells forming at least two stacked first and second cell layers, wherein the first cell layer is spaced apart from the second cell layer by a plurality of bucklable, elastic structural components structurally linked to the cells and configured to buckle upon the inflation or deflation of the cells to result in a movement of the artificial limb element; a plurality of secondary structural components disposed between cells in each of the first and second cell layers and structurally linked to the cells and configured not to buckle upon the deflation of the plurality of cells; wherein the cells, bucklable structural elements and secondary structural elements are positioned and arranged so that a secondary structural component of the first layer is positioned above a cell of the second layer and a secondary structural element of the second layer is positioned below a cell of the first layer; and the cells are configured for connection with a fluid inflation or deflation source.

In some embodiments, the artificial skeletal muscle system is an artificial arm or leg or a hard artificial skeleton of any part of the human or animal body. More generally, as the muscles of human and other animals are mostly functionally linear actuators, the soft buckling linear actuator (e.g., BAM) can mimic the kinetic configuration of all structures on human or other animals that involves one or more muscles. In short, the soft buckling linear actuators are functionally equal to natural muscles. In some embodiments, the soft buckling linear actuators are anchored to artificial skeletons that are humanoid or animal like, and actuated to generate a contraction which moves the skeleton in a biomimetic way. Non-limiting examples of application include: artificial arms that lift, artificial legs that walk, artificial hands that grasp, etc. Movements in structures that consists of the soft buckling linear actuators and hard "skeletons" are not limited to natural occurring structures in animals; more generally the motions may include, but are not limited to: translational motions, pivoting and rotating motions, gripping and releasing motions, opening and closing motions, contraction and extension motions, a compound motion that is a combination of some of the above mentioned motions, etc.

In yet another aspect, a soft robotic machine, including:
a soft machine element; and
a soft buckling linear actuator of any one of embodiments described herein and connected to the soft machine element, wherein upon the inflation or deflation of the cells, the soft buckling linear actuator generates a linear force so that the soft machine moves to mimic a human or animal-like motion or structure.

In another aspect, at least partially soft structures or fully soft structures can be made with soft buckling linear actuators without involvement of hard skeletons. As examples, a soft robotic machine is described. The soft robotic machine includes a soft machine element; and one or more soft buckling linear actuators described herein and connected to the soft machine element. The soft machine element can be another soft buckling linear actuator, a hard or soft body part, or a pneumatic expansion actuator. Non-limiting examples of the soft robotic machine include a soft robotic millipede and a tube-climbing robot. The former (millipede) includes a plurality of soft buckling linear actuators according to one or more embodiments described herein. The latter (tube climbing robot) includes one soft buckling linear actuator unit as described herein with two pressure actuated pneumatic actuator on each ends of the soft buckling linear actuator.

In certain embodiments, the soft actuating device is a soft robotic climber, a soft robotic worm or millipede, or an artificial limb including a BAM, as described herein.

Soft Buckling Linear Actuator

As described herein, we explored buckling in elastomers—usually considered a mechanism of failure in structures—as a mechanism to achieve complex, reversible, and nonlinear motions. In certain embodiments, the structures described herein (vacuum-actuated muscle-mimetic pneumatic (VAMP) structures) are based on a new mechanism for actuation, in which the muscle-mimetic characteristics of this motion come from applying negative pressure (vacuum) to the structure, and in which this motion derives from the cooperative collapse (that is, buckling) of a set of elastomeric beams or pillars. In certain embodiments, we describe the design of VAMPs that generate linear motions with strain up to 45%, and tensions up to at least 6.5 N/cm$^2$, both of which are similar to those of human muscle (typical strain of 20%, and maximum up to ~40%; maximum sustained tension of 10 N/cm$^2$, and maximum impulsive tension of 35N/cm$^2$).

In certain embodiments, the actuators described herein are based on an elastomeric slab with holes that are sealed with an elastomeric membrane. The holes are interconnected by—ultimately to an external pneumatic port—small channels that allow them to be evacuated. This design allows ambient pressure to be applied isotropically to the device on evacuation. These structures can be considered as an ensemble of elastomeric beams or pillars. The application of vacuum causes the reversible, cooperative buckling of these pillars, and results in motion of the actuator. This design converts pressure-volume work (done when applying negative pressure) into mechanical work (here, for example, lifting a weight as the slab changes shape).

In certain embodiments, the bucklable, elastic structural component has an axis along its long dimension and buckles in a direction perpendicular to the axis, or about 90 degrees to the axis (e.g., from 80-90, 85-90, 85, 86, 87, 88, 89 or 90 degrees). In other embodiments, the bucklable, elastic structural component has an axis along its long dimension and buckles in a direction at any angle to the axis. This may be accomplished by disposing the bucklable, elastic structural component at an angle other than 90 degree relative to the long axis of the secondary structural components. Non-limiting examples of angles include 75, 80, or 85 degrees, or in any range bounded by any two values disclosed herein.

Soft Actuating Device Arrays

In another aspect, a soft actuating device array is described, including a plurality of the soft actuating devices of any one of the embodiments described herein. In certain embodiments, the array comprises a plurality of the soft actuating devices described herein, and the cell/pillars are arranged to result in actuations in a predetermined pattern. In certain embodiments, each of the soft buckling linear actuators is connected to the same external fluid or vacuum source. In other embodiments, at least two of the soft buckling linear actuators are connected to different external fluid or vacuum sources capable of being activated independently.

Method of Actuation

In yet another aspect, a method of actuation is described, including: providing the soft buckling linear actuator of any one of the embodiments described herein; and deflating the cells or over-inflating the cells to cause the bucklable, elastic structural component to buckle to generate a linear force.

In some embodiments, the method further includes causing the soft buckling linear actuator to contract or expand. In some embodiments, causing the soft buckling linear actuator to contract includes deflating the cell(s) to cause the bucklable, elastic structural component to buckle to generate a contracting force. In other embodiments, causing the soft buckling linear actuator to expand includes over-inflating the cell(s) to cause the bucklable, elastic structural component to buckle to generate an expansion force.

In yet another aspect, a method of actuation is described, including: providing the soft actuating device or the soft actuating device array of any one of embodiments described herein; and deflating the cells or over-inflating the cells of the plurality of the soft actuators to cause the bucklable, elastic structural component to buckle to generate a linear force available for actuation. The cells of the plurality of the soft buckling linear actuators can be deflated or over-inflated together or independently. In some embodiments, the soft actuating device includes a plurality of the cells, and the cells can be deflated to cause the soft actuating device to contract. Alternatively, the cells can be re-inflated or over-inflated to cause the soft actuating device to expand.

Artificial Muscle

In some embodiments, the soft buckling linear actuator described herein is a buckling artificial muscle. The buckling artificial muscle described is based on a new mechanism for actuation, in which motion comes from applying negative pressure (vacuum) to the structure, and in which this motion derives from the cooperative collapse (that is, buckling) of a set of elastomeric beams or pillars. We refer to these actuators as "buckling artificial muscle" (BAM) or VAMP. As a demonstration, we describe the design of BAMs that generate linear motion with strain up to 45%, and specific tension potentially up to 10 N/cm$^2$, which is similar to that of a human muscle (~30%, 10~15N/cm$^2$).

In certain embodiments, the system developed herein to operate BAMs uses negative pressure for actuation. In certain embodiments, the soft buckling linear actuators, e.g., BAMs, include elastomeric beams or pillars fabricated in an elastomeric solid; the application of vacuum causes the reversible, cooperative buckling of these pillars, and the motion of the actuator. In certain embodiments, the soft buckling linear actuators utilize pressure applied isotropically to the device by evacuating it, e.g., using a network of channels, and coupling the buckling of the pillars to the collapse of structures connecting them under the influence of the atmospheric pressure external to the system. This type of design converts pressure-volume work (done by applying negative pressure) into mechanical work (here, for example, lifting a weight).

Any combination of one or more soft buckling artificial actuators described herein and hard skeletons that generate mammalian-like or novel motions is contemplated. The one or more soft buckling linear actuators can optionally be combined with other kinds of soft actuators (e.g., expansion-mode pneumatic actuators), or be included in a machine that is completely or almost completely soft.

Characterizations of BAM

In certain embodiments, two relationships for BAMs are characterized as those between i) applied negative pressure and change in length; and ii) the Young's modulus of the elastomeric material and the maximum weight the structure can lift (that is, the force it can apply).

In the first characterization, we first define two variables: 1) the difference in pressure, $\Delta P$, between the external ambient pressure $P_{ext}$ (typically ~1 atm=100 kPa) and the pressure inside the chambers $p_{int}$ when under vacuum (Eq. 1):

$$\Delta P = P_{ext} - P_{int} \qquad (1)$$

2) The loading stress resulting from hanging weight on VAMPs $\sigma$ (in kPa) is defined by the force in the direction of actuation T divided by cross-sectional area of the actuator A (Eq. 2):

$$\sigma = \frac{T}{A} \qquad (1)$$

The actuation strain $s(\Delta P', \sigma) s(\Delta P, \sigma)$ is a function of these two variables (Eq. 3), where $L(\Delta P, \sigma)$ is the length of the VAMPs under loading stress $\sigma$ on application of a differential pressure $\Delta P$:

$$s(\Delta P, \sigma) = \frac{L(\Delta P, \sigma) - L(0, \sigma)}{L(0, 0)}. \qquad (1)$$

Figure 2A:
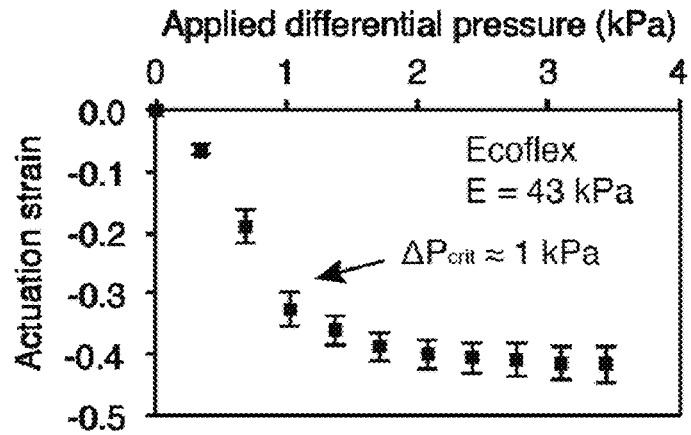
FIG. 2A illustrates a graph of Actuation strain vs. applied differential pressure curves of VAMPs made of Ecoflex (E=43 kPa) and Elastosil (E=520 kPa) at no load, according to one or more embodiments described herein.

FIG. 2A shows the actuation strain of VAMPs under zero loading stress $s(\Delta P, \sigma)$. As the differential pressure $\Delta P$ increases, the VAMPs contract along their long axis, initially approximately linearly. Above a certain value ($\Delta P_{crit}$) of $\Delta P$, which depends on the properties of the elastomer, the VAMPs collapse almost completely. For Ecoflex 00-30 (Young's Modulus E=43 kPa), $\Delta P_{crit}$ is about 1 kPa; for Elastosil M4601 (E=520 kPa), $\Delta P_{crit}$ is about 10 kPa. This critical differential pressure is proportional to the Young's modulus of the material (for detailed theoretical discussion below). Hence VAMPs made of a material with Young's modulus E≈4 MPa will have a $\Delta P_{crit}$ of ~100 kPa (1 atm). A VAMP made of an elastomer with this high stiffness has a projected loading stress of about 60 kPa (or 6 N/cm$^2$) at 30% actuation strain, and a loading stress of about 100 kPa (or 10 N/cm$^2$) at 0% actuation strain. This scaling rule describes the stiffness of the material from which VAMPs can be fabricated. VAMPs made from materials with E>4 MPa will not actuate fully under atmospheric pressure, but if $P_{ext}$ is greater (e.g., in undersea applications), much greater forces could be generated, using stiffer elastomers.

Figure 2B:
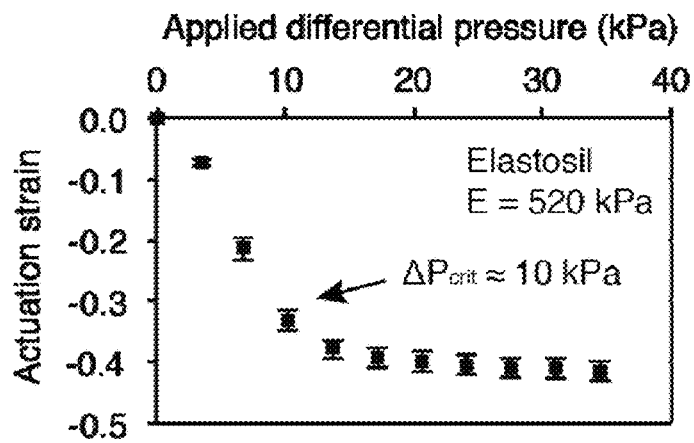
FIG. 2B shows the loading stress vs. actuation strain curves of VAMPs made of Ecoflex (E=43 kPa) and Elastosil (E=520 kPa), while a differential pressure of ΔP=90 kPa is applied, according to one or more embodiments described herein.

FIG. 2B shows the actuation strain $s(\Delta P, \sigma)$ of VAMPs made from two different elastomers as a function of loading stress $\sigma$, while applying a negative pressure greater than $\Delta P_{crit}$. The maximum loading stress (a.k.a. specific tension) determines the maximum weight VAMPs fabricated in a given elastomeric material can lift. The specific tension of VAMPs scales linearly with the Young's modulus of the actuator (For detailed theoretical discussions see the SI).

Figure 3A:
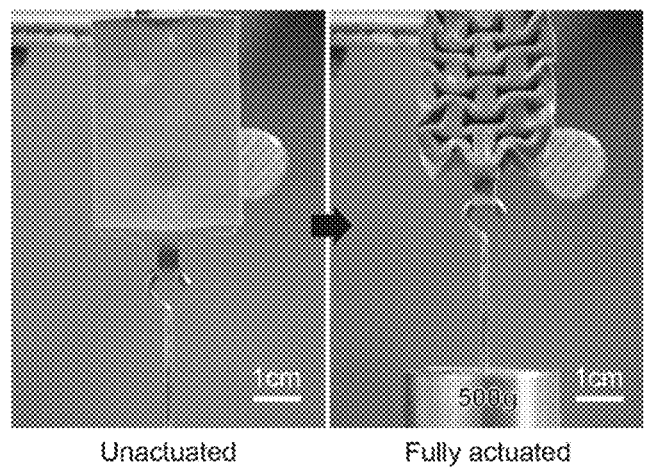
FIGS. 3A-3B shows a buckling artificial muscle (BAM) made from stiffer elastomers lifting weights, according to one or more embodiments described herein.
Figure 3B:
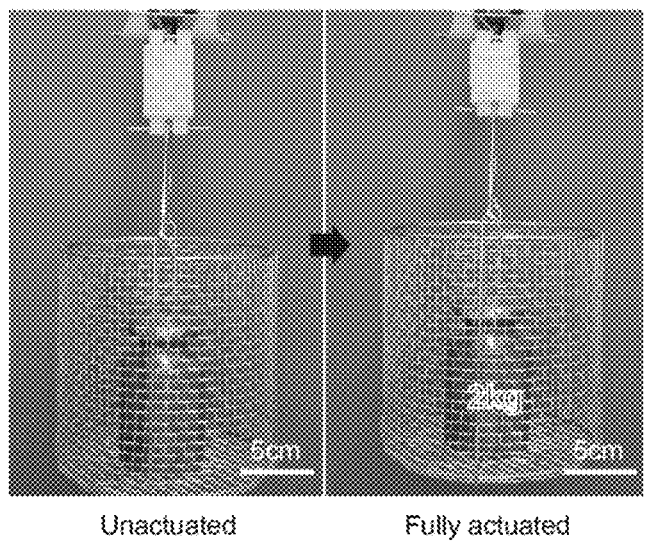

FIGS. 3A to 3B show that VAMPs with indistinguishable geometrical sizes and shapes (34 mm×28 mm×46.5 mm) support higher maximum loads, as the stiffness of the elastomer they are made from increases. We have experimentally demonstrated up to 65 kPa loading stress with high stiffness materials (Stratasys PolyJet 3D printed soft material with a Young's modulus of E≈2.5 MPa, FIGS. 8A-8B.

Specifically, in certain embodiments, a BAM is shown lifting a much higher weight (500 g; FIG. 3A). The highest stiffness that atmospheric pressure can actuate is approximately a Young's modulus of E=4 MPa. A BAM made of this stiff material has a projected a loading stress of about 60 kPa (or 6N/cm$^2$) at 30% actuation strain, and a loading stress of about 100 kPa (or 10N/cm$^2$) at 0% actuation strain. Specific tension is the effective physical pressure that the actuator can generate. FIG. 3B shows a BAM of the same geometry, but made of Stratasys PolyJet 3D printed soft material (E~1.6 MPa) lifting an even higher weight (~2.3 kg plus metal basket). It is, therefore, limited by the maximum differential pressure one can apply between the inside and the outside of the BAM—that is, by the atmospheric pressure (~100 kPa)—this pressure provides an intrinsic limit to the specific tension that a BAM can provide.

Demonstration of Muscle-Mimetic Actuation.

In certain embodiments, when vacuum is applied to the internal cells, the BAM contracts uni-axially in a direction determined by its internal, soft, meta-structure (axis a in FIGS. 1B and 1C). This pattern can extend indefinitely, since it is scalable in both the length and the cross-sectional area of the BAM. Increasing the length increases the total displacement of the BAM on actuation, and increasing the cross-sectional area increases the force it generates. In certain embodiments, the BAM as described herein can actuate a human skeleton in a fashion similar to a human bicep. To demonstrate the use of a BAM to mimic the motion of a human bicep, we designed a structure to bend the (artificial) skeleton of an arm, which lifts an external weight (a volleyball in FIG. 4B).

Figures 4A, 4B:
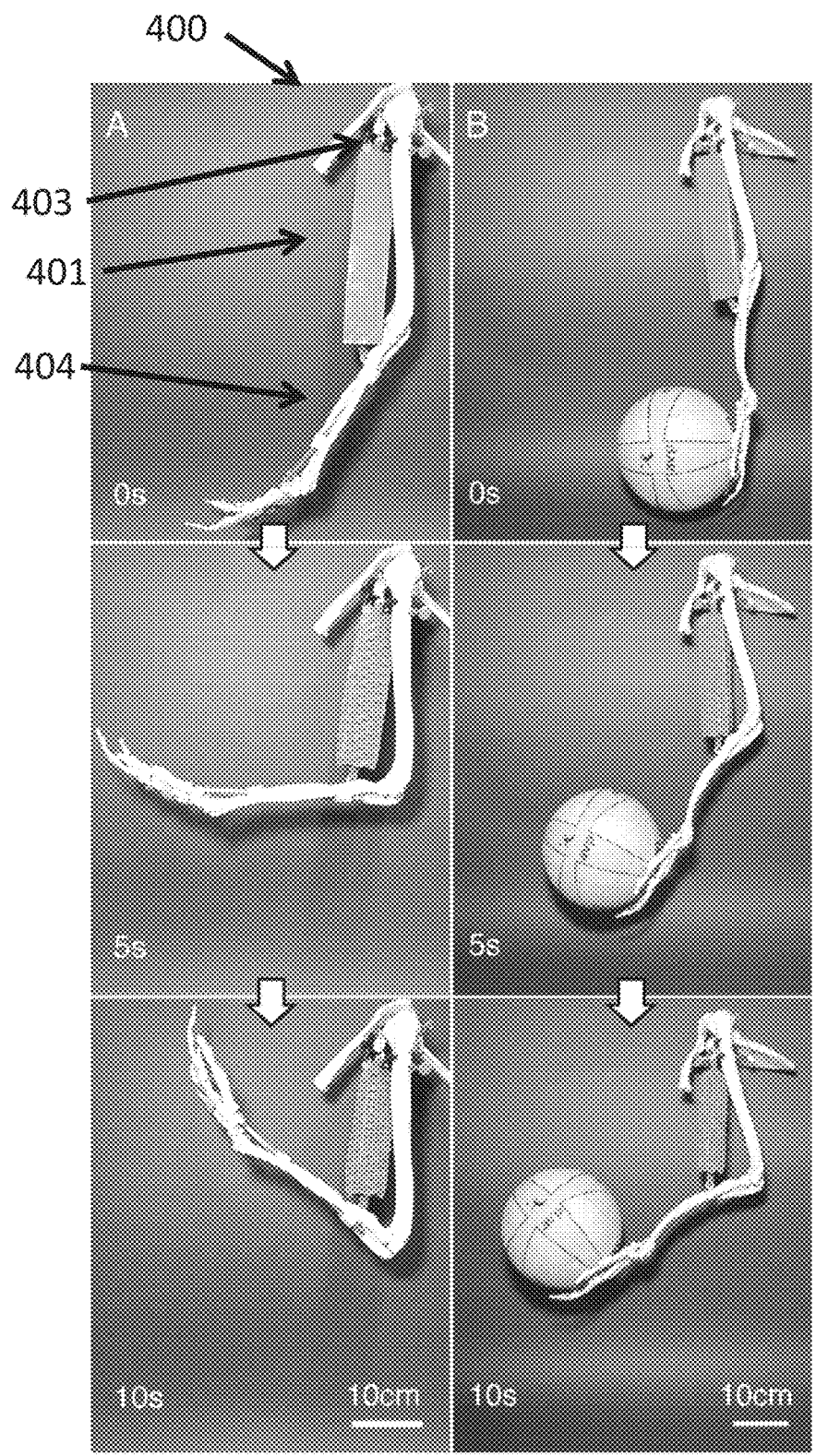
FIG. 4A shows the use of a VAMP to actuate a polymer replicate of the bones of a human arm, with mechanics similar to that employed by a human bicep muscle, according to one or more embodiments described herein.
FIG. 4B shows the VAMP-actuated "arm" lifting a volleyball, which has a standard size and weighs 274 g (scale bars are 10 cm), according to one or more embodiments described herein.

When vacuum is applied to the internal chambers, the VAMPs contract uniaxially in a direction determined by their internal soft structure (FIG. 1B). This pattern can extend over substantial lengths and areas. Increasing the length increases the total displacement of the VAMPs on actuation, and increasing the cross-sectional area increases the force they generates. Readily accessible geometries provide properties (speed, strain) on actuation that mimic human muscle. FIGS. 4A-4B demonstrates the ability of an artificial skeletal muscle system 400 including a soft buckling linear actuator (e.g., VAMP 401) and man-made skeleton 404 to mimic the motion of human biceps. Metal wires in rubber tubing 403 served as tendons to connect the VAMP 401 to the skeleton 404. In FIG. 4A, the length of the VAMP 401 decreased by ~30% on actuation (as shown by time-lapsed photos at 0, 5, and 10 seconds); the resulting movement of the "hand" was about five times the change in length of the VAMP, because of an lever arm ratio of 1:5. We chose this value to resemble that of a human arm (which is around 1:4.9). In FIG. 4B, the VAMP is shown to lift a volleyball by time-lapsed photos at 0, 5, and 10 seconds.

VAMPs can demonstrate high strain rates by fabricating them to have a wide pneumatic port (for gas transfer), as air friction in the port is the main limiting factor of actuation speed. We have demonstrated strain rate up to 45%·s$^{-1}$ with VAMPS. This value is similar to that of a human skeletal muscle (~50%·s$^{-1}$).

Applications in Various Systems and Parallel Actuation of the Soft Buckling Linear Actuators In certain embodiments, the soft actuating device includes a plurality of the soft buckling linear actuators. Each unit of the soft buckling linear actuator is capable of individual linear actuation; however, that motion is linked to and in synchrony with the motion of the units in the array. This has been demonstrated in the soft robotic worm (FIGS. 5A-5B) and the soft robotic climber (FIGS. 6A-6B), described below.

Figure 5A:
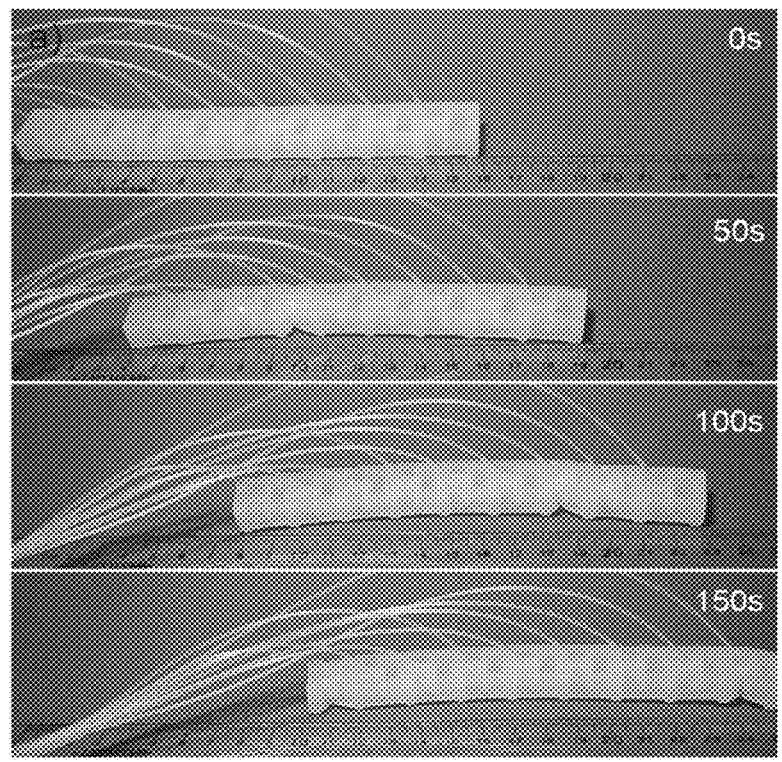
FIG. 5A shows a soft robotic worm including multiple buckling linear actuators and the time-lapsed snapshots of its movement, according to one or more embodiments described herein.
Figure 5B:
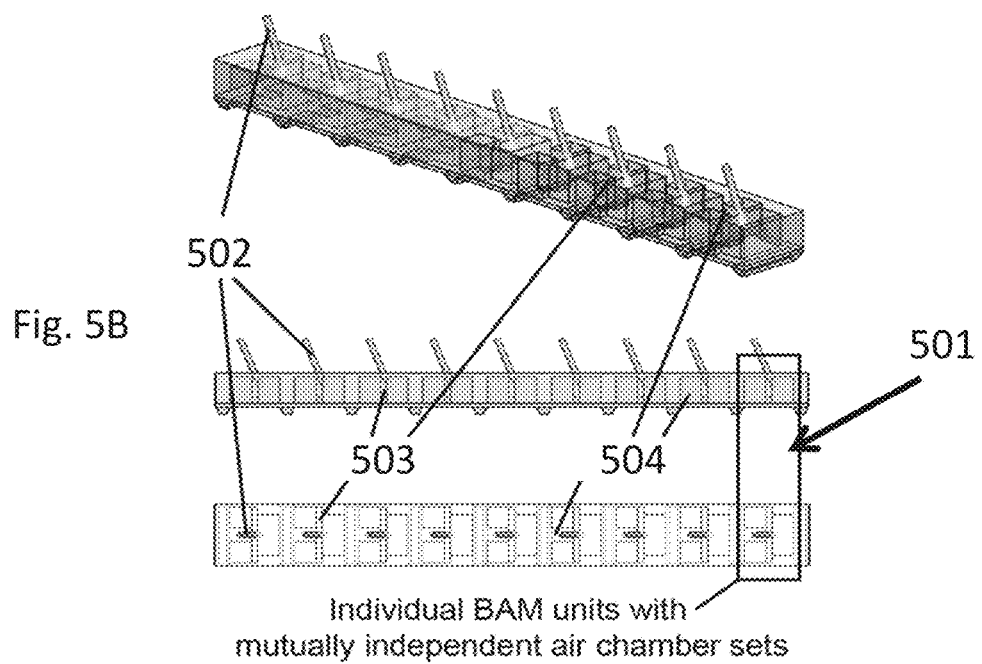
FIG. 5B provides a schematic illustration of this worm with multiple buckling linear actuator units, according to one or more embodiments described herein.

The soft buckling linear actuator described herein, e.g., BAMs, can be utilized in a variety of forms of soft robotic devices such as soft robots or artificial limbs. The soft actuating device as described herein may be structures without rigid structures or predominantly formed by soft body's portions. For example, it can mimic the movements of invertebrates that contract their body for locomotion (e.g., earthworms and millipedes), by having multiple BAM units in series. As shown in FIG. 5A, BAMs can be stacked in a series to generate more complex functions. Here, a plurality of BAMs is assembled together and actuated in sequence to make a soft robotic worm that generates worm-like peristalsis motion. FIG. 5A shows the snapshots of the movement of the soft robot worm at 0, 50, 100, and 150 seconds. Alternatively, the soft actuating device as described herein may include rigid structures or rigid body portions to achieve a variety of functions. FIG. 5B shows the schematics of the millipede, which includes a plurality of pneumatic vacuum inputs 502 and BAM units 501. Each BAM unit is connected to a different pneumatic vacuum unit to allow it to be actuated independently. Each BAM unit includes one or more bucklable, elastic structural components, e.g., horizontal walls 503 (which buckles during actuation), and one or more secondary structural components, e.g., vertical walls 504 (which are configured not to buckle).

In certain embodiments, the vacuum-operated BAM can be used in conjunction with pressure based soft actuators to realize more complex functions. As shown in FIG. 6A, a contracting soft buckling linear actuator, e.g., BAM unit (601 shown in FIG. 6B), is sandwiched between two expanding soft actuators, e.g., pneumatically actuated expanding disks 602 and 603. The three actuation-units are actuated in a particular sequence to generate a soft robotic worm with an inchworm like motion, which enabled the combined system to climb up a tube. Specifically, the expanding actuator acts 602 and 603 as feet to cling on to the interior of the tube via expansion upon pneumatic inflation, while the contracting unit 601 adjusts the distance between the two "feet", so that the robot can inch forward—a motion similar to that of an inchworm (FIG. 6B). FIG. 6A shows the snapshots of the movement of the soft robotic worm at 0, 0.5, 1, 1.5, and 2 seconds. FIG. 6B shows the schematics of the worm, including two expansions rings 602 and 603 at either end of the BMA unit 601. The two expansion rings 1 and 2 and the BAM unit may each be connected to a separate inflation devices 604. The BAM unit has a similar design as the one shown in FIG. 1A.

BAMs offer a new approach, and a new mechanism for, biomimetic actuation having significant similarity to biological muscle. Their key features are i) no expansion in volume on contraction; ii) moderately rapid actuation (one second for full-scale actuation of the structures shown in FIGS. 1 and 2; and iii) "cooperativity:" because they use soft materials, and because they are intrinsically compliant, they are (to use the term common in robotics) cooperative, and can be used safely and synergistically with humans; their motion (at least in the systems that we have demonstrated) cannot cause harm. The thermodynamic efficiency of transduction of the pressure-volume work required to actuate them into mechanical (force×distance) work (e.g., lifting a weight) is limited by dissipation of the work required to strain the system into heat in the elastomer, and can be near 100% if made from non-viscoelastic materials. They are sufficiently inexpensive to fabricate that they could be considered for single-use applications.

Figure 2B:
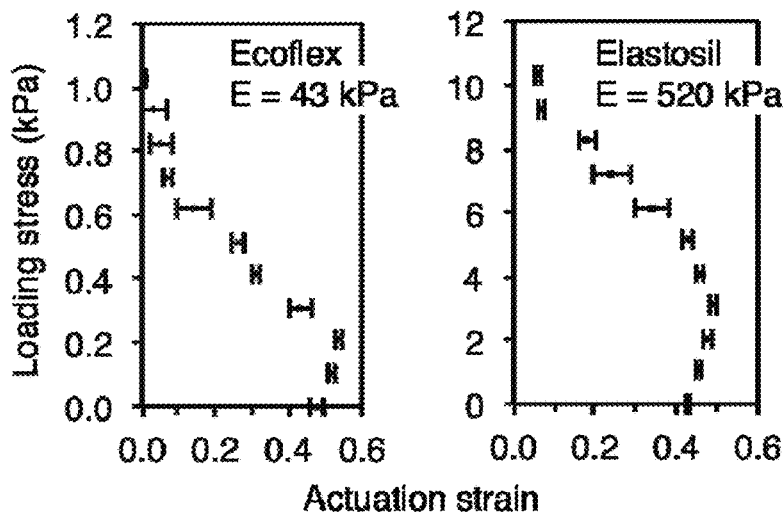

The designs that we use in the actuators in FIGS. 1, 2 and 4 are a small subset of those that can be created through appropriate designs of the patterns of pillars making up the BAM, and through extension of these quasi-two-dimensional structures into three dimensions. The key feature, however, and all of these designs is the constructive use of buckling in an elastomeric material as a feature leading to actuation. Buckling—in rigid structural materials—is usually a mechanism of failure. The ability to exploit buckling to achieve complex, nonlinear motions, reversibly, in elastomers, opens the door to the design of entirely new classes of actuators.

Transfer of Force From the Buckling Structure to Hard Elements

In certain embodiments, the soft actuating device further includes a hard body portion. The soft actuating device can include both soft and hard components to perform useful functions. The soft actuating device is a promising new element one can use in making soft machines or soft and hard hybrid machines.

Materials and Methods
Fabrication of the VAMPs

Figure 7:
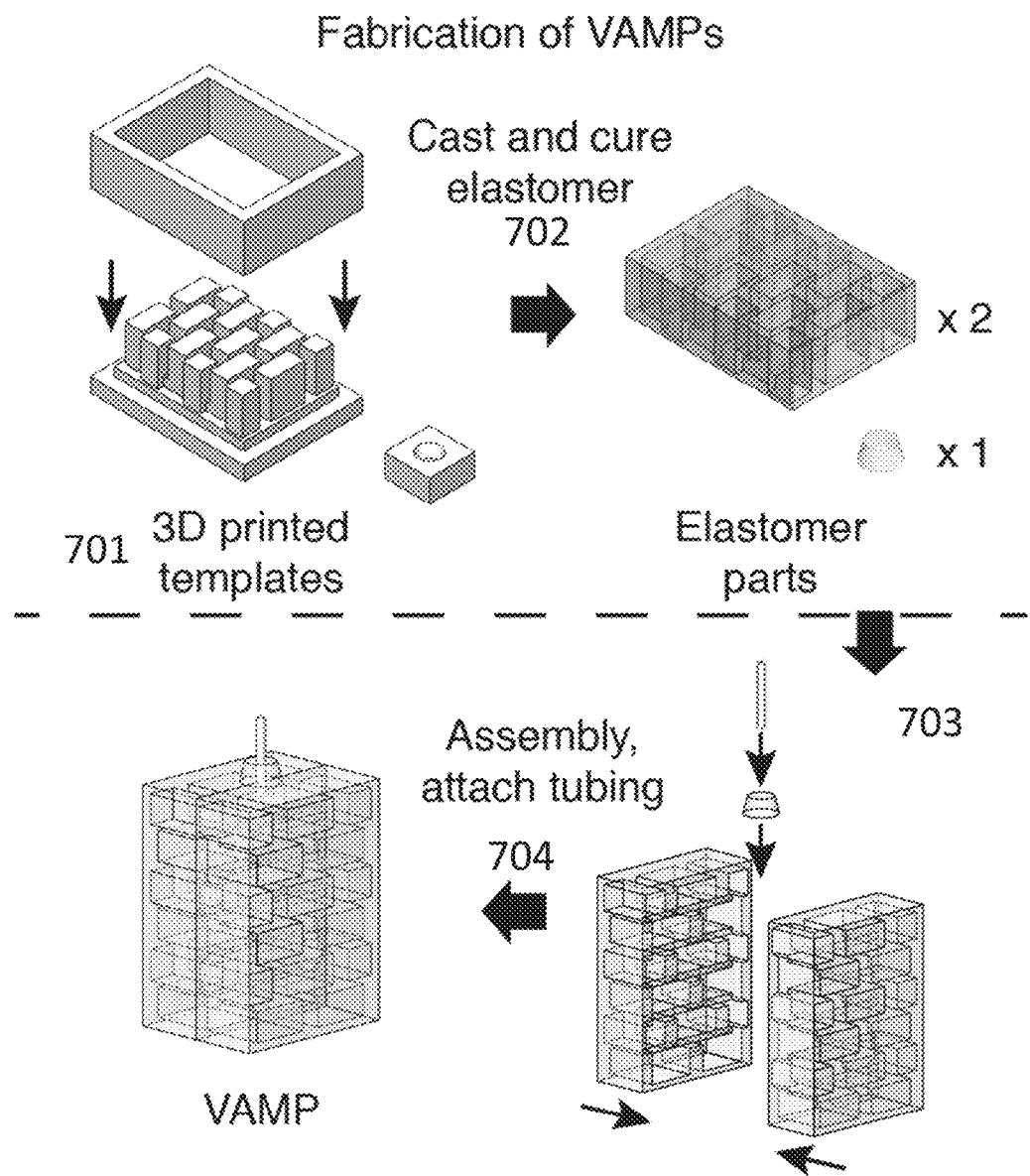
FIG. 7 illustrates a fabrication process of a VAMP, according to one or more embodiments described herein.

The VAMPs were created by replica-molding (FIG. 7). We designed the molds using computer-aided design (CAD) (Solidworks) and fabricated them with acrylonitrile butadiene styrene (ABS) plastic using a 3D printer (StrataSys Fortus 400 mc; Step 701). Curing a silicone-based elastomer (Ecoflex 0030 or Elastosil) (Step 702) against the molds at room temperature (3 hours for Ecoflex 0030 and 6 hours for Elastosil) produced two halves of the VAMPs. These two halves were aligned and bonded together by applying uncured elastomer at their interface prior to placing them in an oven and curing at 60° C. for 10 minutes (Step 703). A conically shaped piece of the elastomer was bonded to the top of the actuator to provide additional material that allowed tubing (Intramedic polyethylene tubing, ID 0.76 mm) to be securely attached to the structure (Step 704). The conical piece was first pierced by a cannula. The tubing was fed through the cannula, which was then removed to leave the tubing imbedded in the VAMP. The tubing was secured through elastic force of the elastomer, which attempts to close the hole occupied now by the tubing.

Figure 8A:
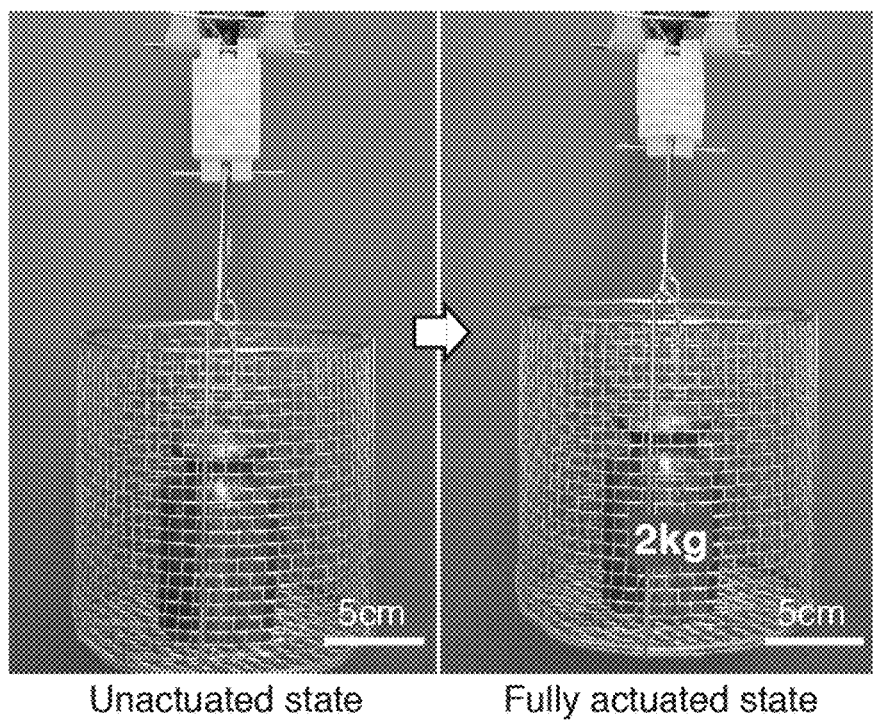
FIG. 8A shows a VAMP of the same geometry as in FIG. 1C, but fabricated in Stratasys PolyJet 3D printed material (E≈2.5 MPa at 50% strain; the material is viscoelastic) lifts a large weight (2 kg), according to one or more embodiments described herein.
Figure 8B:
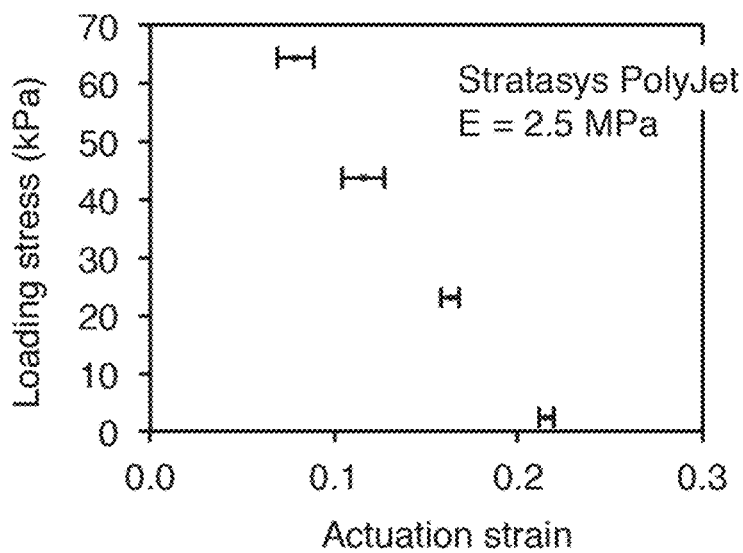
FIG. 8B shows a graph of loading tension as a function of actuation strain for VAMPs fabricated in Stratasys PolyJet 3D printed material with a differential pressure applied set to ΔP=90 kPa, according to one or more embodiments described herein.

In certain embodiments, a strong VAMP was made. FIGS. 8A-8B demonstrate the force generated by a VAMP made from a high stiffness material. Specifically, FIG. 8A shows a VAMP using the same geometry as in FIG. 1C, but fabricated in Stratasys PolyJet 3D printed material (E≈2.5 MPa at 50% strain; the material is viscoelastic) lifts a large weight (2 kg). FIG. 8B shows that the loading tension as a function of actuation strain for VAMPs fabricated in Stratasys PolyJet 3D printed material. The differential pressure applied is set to ΔP=90 kPa.

Theoretical Discussion of Young's Modulus vs. Tension Output

Without wishing to be bound by any particular theory, it is believed that the critical differential pressure ($\Delta P_{crit}, \Delta P_{crit}$)

is proportional to Young's modulus at zero loading stress. We represent the elastomer using the neo-Hookean model. Assuming the elastomer is incompressible, the model indicates that the stress-strain relation contains a single material constant—the Young's modulus E. Let $\Delta P$ be the difference in the pressure between that in the ambient and that inside the actuator. In the absence of the applied load, the differential pressure $\Delta P$ relates to the actuation strain s by $$\Delta P = E f(s) \tag{S2}$$

This relation is obtained on the basis of dimensional considerations. The function $f(s)$ is nonlinear in strain, and depends on ratios of various geometric features (but is independent of the size of the features). If we make two actuators of identical geometric features, but of materials with different Young's moduli, we can plot $\Delta P/E$ as a function of s, and the two curves will fall on top of each other.

When $\Delta P/E$ is large, the cells in the actuator collapse, and the actuation strain reaches a plateau. Critical differential pressure $\Delta P_{crit} \Delta P_{crit}$ is reached when actuation strain reaches near maximum: $s_{max} \approx 0.4$. Plugging into equation S1, we obtain linear relationship between critical differential pressure $\Delta P_{crit}$ and Young's modulus E:

$$\Delta P_{crit}/E = f(s_{max}) = c \tag{S3}$$

where c is a constant. The experimentally determined shape of the function $f(s)$ is given in FIG. 2. Our experimental data shows that $c \approx 0.025$.

Without wishing to be bound by any particular theory, it is believed that the specific tension $\sigma$ is proportional to Young's modulus at a fixed actuation strain. Let $\sigma$ be the nominal stress due to the hanging weight—that is, $\sigma$ is the weight T divided by the cross section area A of the undeformed actuator. Under the neo-Hookean model, we may obtain the following relationship on the basis of dimensional considerations:

$$s = g(\Delta P/E, \sigma/E) \tag{S4}$$

If we make two actuators of identical geometric features, but of materials with different Young's moduli, we can plot s as a function of $\Delta P/E$ and $\sigma/E$. The two surfaces will fall on top of each other.

When $\Delta P/E$ is large, the cells in the actuator collapse, and the actuation strain reaches a plateau. In this case, s become independent of $\Delta P/E$ and only a function of $\sigma/E$:

$$s = h(\sigma/E) \tag{S5}$$

Therefore, at fixed actuation strain $s^*$, the relationship between the specific tension $\sigma$ and Young's modulus is linear:

$$\sigma/E = h^{-1}(s^*) = c^* \tag{S6}$$

where $c^*$ is a constant depending on the value of $s^*$.
Specific Tensions for VAMPs Made of Different Elastomers A VAMP made of Ecoflex 0030 (represented in FIGS. 1C and 3A, E=43 kPa) supports a loading stress of about 0.5 kPa (or 0.05 N/cm$^2$) at 30% actuation strain, and a loading stress of about 1 kPa (or 0.1 N/cm$^2$) at 0% actuation strain. A VAMP made of Elastosil M4601 (represented in FIG. 1D, E=520 kPa) supports a loading stress of about 6 kPa (or 0.6 N/cm$^2$) at 30% actuation strain, and a loading stress of about 10 kPa (or 1 N/cm$^2$) at 0% actuation strain.
Young's Modulus Tests for Different Elastomers The Young's moduli of the Elastomers were measured with standard dog-bone shaped samples in an Instron. The samples were stretched at a strain rate of 0.5 mm/s until rupture. The modulus was estimated by linear fitting the stress strain data from 0 to 50% strain. The slope of this fitting was extracted as an estimate for Young's Modulus.
Speed of Actuation VAMPs demonstrate moderately rapid actuation. Complete actuation of the structures shown in FIG. 1C using a pneumatic pressure line with a 0.75 mm inner diameter and 10 cm in length takes ~1 second. The actuation speed is limited by the diameter of the pneumatic port, as losses due to sheer friction of the air with the tubing is the main factor limiting the actuation speed. Larger VAMPs with the same size of the pneumatic port will actuate more slowly, as the actuation speed is inversely proportional to volume of air that must be removed. The actuation speed can thus be increased for desired applications with gas transfer pressure lines with greater diameter.
Specifications for the Muscle-Mimetic Demo We estimated the force required to lift the lower part of the skeleton (10 kN), the cross sectional dimensions of the VAMP (50 mm×40 mm), and the material (Elastosil) required to generate this force based on equation S5. The VAMP was 240 mm so that the "arm" could achieve the required range of movement.
Muscle-Mimetic Demo With Greater Speed In another embodiment, another muscle-mimetic demo was made with a wider pneumatic port (ID=2 mm), which resulted in much faster actuation. The total time required for the "arm" to change from the unactuated state to the actuate state is under one second. One may use a port of greater diameter to achieve even faster motion.
Measurement of Thermodynamic Efficiency The thermodynamic efficiency of transduction of the pressure-volume work required to actuate VAMPs into doing mechanical (force×distance) work (e.g., lifting a weight) is limited by the work required to compress the elastomer. We estimate the thermodynamic efficiency to be 27% for an actuation strain of 20% at 500 g load for the VAMP shown in FIG. 3A. This value is comparable to that of a human skeletal muscle (~40%). The energy stored in the deformed, elastomeric components (which is not converted into useful mechanical work and thus reduces thermodynamic efficiency for a single, unidirectional motion) can be partly recovered during unloading. Therefore a system containing VAMPs can demonstrate greater efficiency over multiple actuation cycles than that measured in a single loading. Similar energy recovery is demonstrated in a number of actuators.

Figure 9A:
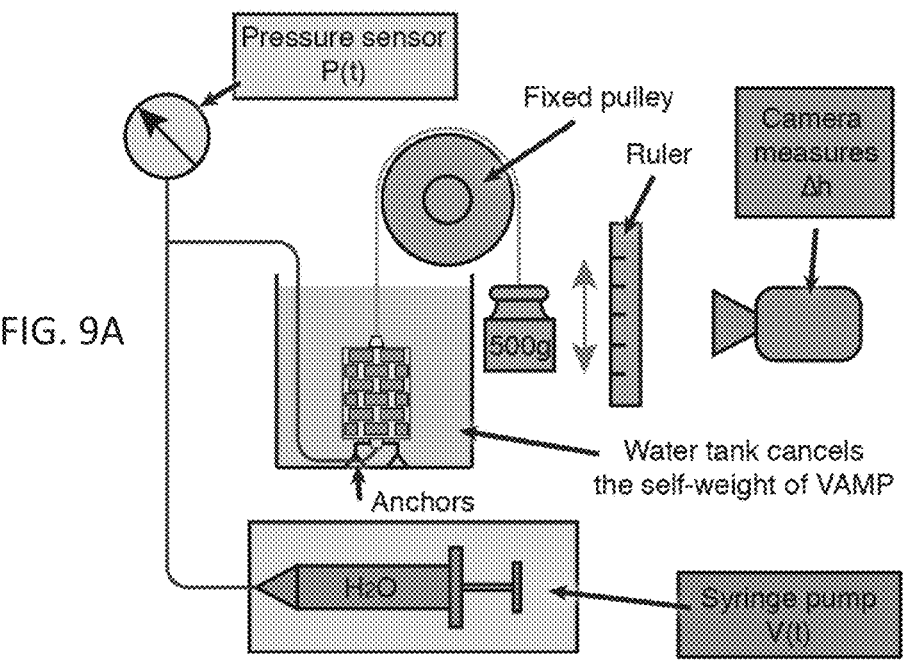
FIG. 9A shows a schematic outline of the experiment used to determine the thermodynamic efficiency of operation of a VAMP, according to one or more embodiments described herein.
Figure 9B:
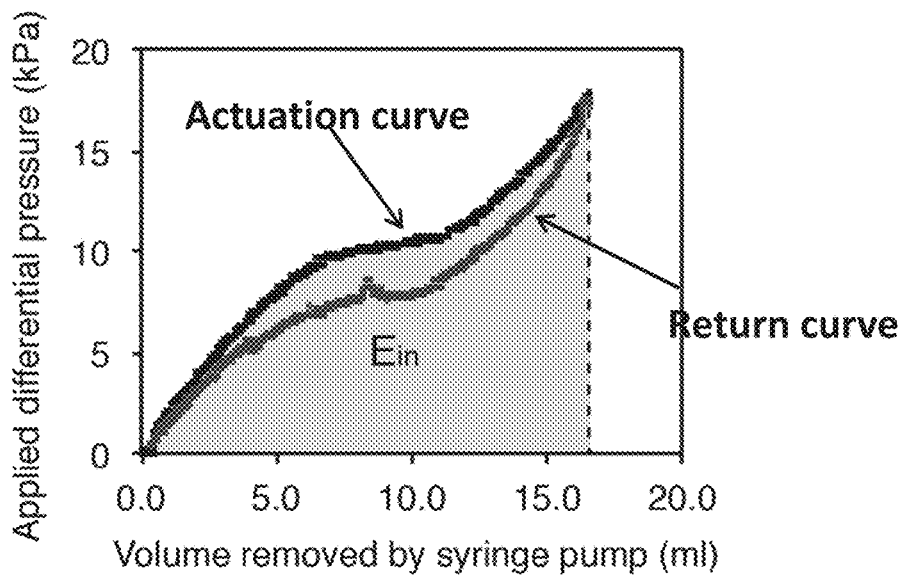
FIG. 9B shows the PV curves of a VAMPs fabricated in Elastosil lifting a 500 g weight, with the shaded area $E_{in}$ indicating the fluidic energy input via the syringe pump, according to one or more embodiments described herein.

We generated PV hysteresis curves by hydraulic inflation and deflation of the actuators with water (an incompressible fluid) in a 1-gallon liquid container. We fixed a syringe pump (Harvard Apparatus, PHD 2000) and a pressure sensor (Transducers Direct, TDH31) in an orientation parallel to the surface of the water (FIGS. 9A-9B, which shows the schematic outline of the experiment used to determine the thermodynamic efficiency of operation of a VAMP). Specifically, FIG. 9A shows the schematics describing the setup used for testing. FIG. 9B shows the PV curves of a VAMP fabricated in Elastosil lifting a 500 g weight. The actuation curve and the return curve are labeled therein. The shaded area $E_{in}$ is the fluidic energy input via the syringe pump.

We clamped the actuator so that it was fully submerged in the water in a vertical position. We filled the actuators with water by submerging them and applying a vacuum several times until bubbles would no longer emerge (squeezing the actuators under water also enabled effective removal of air).

Within each test, we switched from deflation to inflation when the actuator had achieved ~20% contraction. We choose the rate of deflation and inflation to be 0.081 ml/s, which is sufficiently slow to achieve quasi-static conditions. Once the actuator had completed one full cycle and the pressure returned to zero, we deflated it again to assure reproducibility. We repeated this procedure for at least six cycles.

Since the fluid used for inflation/deflation (water) is incompressible, we could equate the volume decrease/increase of fluid in the syringe to that of the increase/decrease in the volume of the channels in the VAMPs. The VAMPs required removal of $V_o$=16.6 ml $V_0$=16.6 ml of water to deflate to its ~20% actuation, creating a lift of $\Delta h$=0.9 mm. $\Delta h$=0.9 mm of a test weight while the applied differential pressure ramped up from 0 kPa to 18 kPa. We calculated the efficiency η by dividing "energy out" $E_{out}$ by "energy in" $E_{in}$:

$$\eta = E_{out}/E_{in} \quad (S7)$$

$E_{out}$ was obtained by calculating the potential energy gain of lifting the weight (m=500 g was the weight we used, and g is the gravitational constant):

$$E_{out} = mg\Delta h \quad (S8)$$

$E_{in}$ was obtained by integrating the differential pressure with respect to volume change:

$$E_{in} = \int_0^{V_0} P(V(dV) \quad (S9)$$

This value is represented by the area under the PV curve (FIG. 9B). Averaging a total of six runs, we obtained an efficiency of η=27%±0.6%.

Measurement of Lifetime

We measured the lifetime of VAMPs fabricated in Elastosil by connecting them to an Arduino controlled/gated pneumatic source. The VAMPs were each fully deflated and then re-inflated to the initial state repeatedly.

Figure 10:
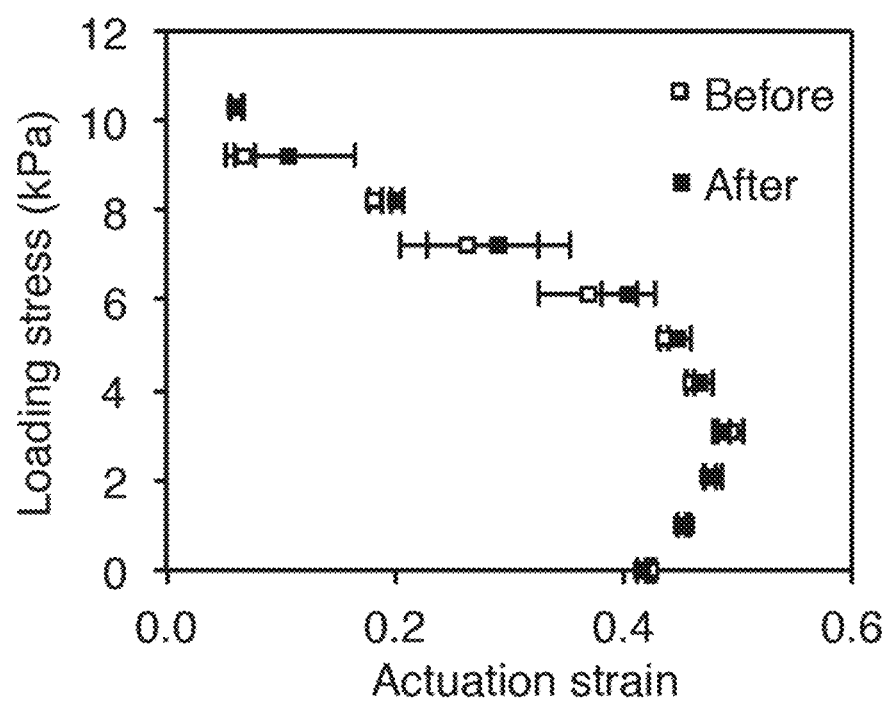
FIG. 10 shows the comparison of the loading stress vs. actuation strain curve of three VAMPs fabricated in Elastosil before and after 1000000 cycles of actuation at 1 Hz, according to one or more embodiments described herein.

The VAMPs were actuated at a frequency of 1 Hz, and left running continuously for ~12 days. This interval resulted in more than 1,000,000 cycles of actuation. We tested the loading stress vs. actuation strain of these three VAMPs, and observed no significant change in the curves (FIG. 10).

As described herein, the soft, buckling linear actuators (e.g., the VAMPs) described here offers a new approach for biomimetic actuation that is the nonlinear motion resulting from cooperative, reversible, buckling and collapse of beams fabricated in an elastomeric polymer. In certain embodiments, the features in the functions of VAMPs include i) no expansion in volume on contraction; ii) performance of actuation similar to many human muscles; iii) "cooperativity:" because they use soft materials, and because they are intrinsically compliant, they are (to use the term common in robotics) cooperative, and can be used safely and synergistically with humans; their motion (at least in the systems that we have demonstrated) cannot cause harm; iv) thermodynamic efficiency that is similar to muscle; v) cost of fabricating that is sufficiently low that they could be considered for single-use applications; vi) performance that is reliable even after high numbers of actuation cycles (VAMPs fabricated in Elastosil demonstrated no significant change in performance after a million cycles of actuation. VAMPs have the potential for long lifetime as a result of two choices of designs: 1) the use of a single material allows the actuator to be fabricated as a single piece, and thus to have no seams or regions of concentrated stress; 2) the maximum strain occurring in the elastomers is also moderate in VAMPs and less than those positive pressure systems subjected to larger strain on inflation. Since the lifetime of elastomers in use usually correlates positively with strain, VAMPs will have longer lifetimes than systems that operate at positive pressure and at high strain.

The designs of the actuators described herein are a non-limiting, a small subset of those that can be created through appropriate design and segmentation of the patterns of pillars making up the VAMPs, and through extension of these quasi-two-dimensional structures into three dimensions. In certain embodiments, the key feature of these designs is the constructive use of cooperative, reversible buckling in an elastomeric material to achieve actuation. The ability to exploit buckling to achieve complex, nonlinear motions, reversibly, in elastomers, opens the door to entirely new classes of actuators with fundamentally new designs. The ability to mimic muscle, in particular, makes biomimetic designs based closely on the anatomy of animals practical.

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

The invention claimed is:

1. A soft buckling linear actuator comprising: a plurality of bucklable, elastic structural components each having its longest dimension along a first axis; wherein each two adjacent bucklable, elastic structural components are at an angle relative to each other of 165-180 degrees; and a plurality of secondary structural components each disposed between and bridging two adjacent bucklable, elastic structural components; wherein at least two adjacent bucklable, elastic structural components and the secondary structural components in-between define a layer comprising a plurality of cells each capable of being connected with a fluid inflation or deflation source; the secondary structural components from two adjacent layers are not aligned along a second axis which is at an angle of 80-90 degrees to the first axis; and the secondary structural components are configured not to buckle, the bucklable, elastic structural components are configured to buckle along the second axis to generate a linear force, upon the inflation or deflation of the cells; wherein the bucklable, elastic structural component is configured to buckle upon the deflation of the cell and return to its original position when the deflated cell is re-inflated.

2. The soft buckling linear actuator of claim 1, wherein the plurality of cells are connected to each other and configured for connection with the same fluid inflation or deflation source but are otherwise isolated from the atmosphere.

3. The soft buckling linear actuator of claim 1, wherein a secondary structural component of a first layer is positioned above a cell of an adjacent, second layer and a secondary structural element of the second layer is positioned below a cell of the first layer.

4. The soft buckling linear actuator of claim 1, wherein the linear force is an expansion or contracting force.

5. The soft buckling linear actuator of claim 1, wherein the bucklable, elastic structural component is made from an elastic polymer.

6. The soft buckling linear actuator of claim 1, wherein the bucklable, elastic structural component is configured to buckle upon the over-inflation of the cell which generates a pressure above the atmosphere pressure and returns to its original position when the over-inflated cell is deflated.

7. The soft buckling linear actuator of claim 1, wherein the bucklable, elastic structural component has high aspect ratio.

8. The soft buckling linear actuator of claim 7, wherein the high aspect ratio is more than 2:1, 3:1, 4:1, 5:1, 10:1, or 20:1.

9. The soft buckling linear actuator of claim 1, wherein the secondary structural component is thicker, shorter and/or more rigid than the bucklable, elastic structural component.

10. The soft buckling linear actuator of claim 1, wherein the fluid is air.

11. The soft buckling linear actuator of claim 1, wherein the cell is in the form of a rod, slit, sphere, cube, hexahedron, or cylinder.

12. The soft buckling linear actuator of claim 1, wherein the bucklable, elastic structural component is in the form of a pillar, a lever, or beam.

13. The soft buckling linear actuator of claim 1, wherein the fluid inflation or deflation source is a gas pump, a gas vacuum, or a gas pump and vacuum.

14. An artificial skeletal muscle system, comprising:
one or more artificial skeletal elements; and
a plurality of the soft buckling linear actuators of claim 1 each connected to the artificial skeletal element;
wherein upon the inflation or deflation of the cells, each of the soft buckling linear actuators generates a linear force so that the artificial skeletal element performs a human or animal-like motion.

15. The artificial skeletal muscle system of claim 14, wherein the artificial skeletal muscle system is an artificial limb, finger, toe, heart, or stomach.

16. A soft robotic machine, comprising:
a soft machine element; and
a plurality of the soft buckling linear actuators of claim 1 each connected to the soft machine element,
wherein upon the inflation or deflation of the cells, each of the soft buckling linear actuators generates a linear force so that the soft machine moves to mimic a human or animal-like motion or structure.

17. The soft robotic machine of claim 16, wherein the soft robotic machine has a whole soft body or a soft body comprising one or more hard portions.

18. A method of actuation, comprising:
providing the soft buckling linear actuator of claim 1; and
deflating the cells or over-inflating the cells to cause the bucklable, elastic structural component to buckle to generate a linear force.

19. The method of claim 18, further comprising causing the soft buckling linear actuator to expand or contract.

20. A method of actuation, comprising:
providing the artificial skeletal muscle system of claim 14; and
independently deflating or over-inflating the cells of the plurality of the soft buckling linear actuators to cause the bucklable, elastic structural components to buckle to generate linear forces and the artificial skeletal muscle system to move to mimic a human or animal-like motion or structure.

21. The method of claim 20, further comprising causing the soft buckling linear actuators to expand or contract.

22. A method of actuation, comprising:
providing the soft robotic machine of claim 16; and
independently deflating or over-inflating the cells of the plurality of the soft buckling linear actuators to cause the bucklable, elastic structural components to buckle to generate linear forces and the soft machine to move to mimic a human or animal-like motion or structure.

23. The method of claim 22, further comprising causing the soft buckling linear actuators to expand or contract.

* * * * *